United States Patent
Peshkin et al.

(10) Patent No.: US 6,198,794 B1
(45) Date of Patent: *Mar. 6, 2001

(54) APPARATUS AND METHOD FOR PLANNING A STEREOTACTIC SURGICAL PROCEDURE USING COORDINATED FLUOROSCOPY

(75) Inventors: Michael A. Peshkin, Skokie; Julio J. Santos-Munné, Evanston, both of IL (US)

(73) Assignee: Northwestern University, Evanston, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/483,107

(22) Filed: Jan. 14, 2000

Related U.S. Application Data

(63) Continuation of application No. 09/020,767, filed on Feb. 9, 1998, which is a continuation of application No. 08/649,798, filed on May 17, 1996, now Pat. No. 5,799,055, which is a continuation of application No. 08/648,313, filed on May 15, 1996, now abandoned.

(51) Int. Cl.[7] .................................................. A61B 6/02
(52) U.S. Cl. ................................................ 378/42; 606/130
(58) Field of Search ................................ 378/41, 42, 62; 606/130

(56) References Cited

U.S. PATENT DOCUMENTS

| | | |
|---|---|---|
| 4,955,891 | 9/1990 | Carol . |
| 5,265,610 | 11/1993 | Darrow et al. . |
| 5,389,101 | 2/1995 | Heilbrun et al. . |
| 5,799,055 * | 8/1998 | Peshkin et al. ................ 378/42 |
| 5,868,673 * | 2/1999 | Vesely ........................... 600/407 |
| 6,069,932 | 5/2000 | Peshkin et al. . |

OTHER PUBLICATIONS

Canny, "A Computational Approach to Edge Detection," IEEE Transaction on Pattern Analysis and Machine Intelligence, vol. 8 (No. 6), pp. 679–698, (Nov. 8, 1986).

Nolte, et al., "A Novel Approach to Computer Assisted Spine Surgery, Proceeding sof the 1st International Symposium on Medical Robotics and Computer Assisted Surgery," pp. 323–328, (Sep. 8, 1994).

Munne, Peshkin, et al., "A Stereotactic/Robotic System for Pedicle Screw Placement, Interactive Technology and the New Paradigm for Healthcare," pp. 326–333, (Aug. 8, 1995).

Viant, et al., "A Computer Assisted Orthopaedic Surgical System for Distal Locking of Intramedullary Nails, University of Hull," p. 8.

Lavallee, et al., "Computer–Assisted Spin Surgery: A Technique for Accurate Transpedicular Screw Fixation Using CT Data and a 3–D Optical Localizer, Journal of Image Guided Surgery," pp. 65–73, (Aug. 8, 1995).

Lavallee, et al., "Computer–Assisted Spine Surgery: A Technique for Accurate Transpedicular Screw Fixation Using CT Data and a 3–D Optical Localizer, Proceedings of the 1st International Symposium on Medical Robotics and Computer Assisted Surgery," pp. 315–321, (Sep. 8, 1994).

Finlay, "Orthosista An Active Surgical Locliser for Assisting Orthopaedic Fracture Fixation," pp. 203–207.

P. Potamianos, et al., "Intra–Operative Registration for Percutaneous Surgery," pp. 156–164.

* cited by examiner

*Primary Examiner*—David V. Bruce
(74) *Attorney, Agent, or Firm*—Marc A. Hubbard; Munsch, Hardt, Kopf & Harr, P.C

(57) ABSTRACT

An apparatus and method is provided for coordinating two fluoroscope images, which permits accurate computer-based planning of the insertion point and angle of approach of a needle, drill, screw, nail, wire or other surgical instrumentation into the body of a patient, and subsequently guides the surgeon in performing the insertion in accordance with the plan.

55 Claims, 28 Drawing Sheets

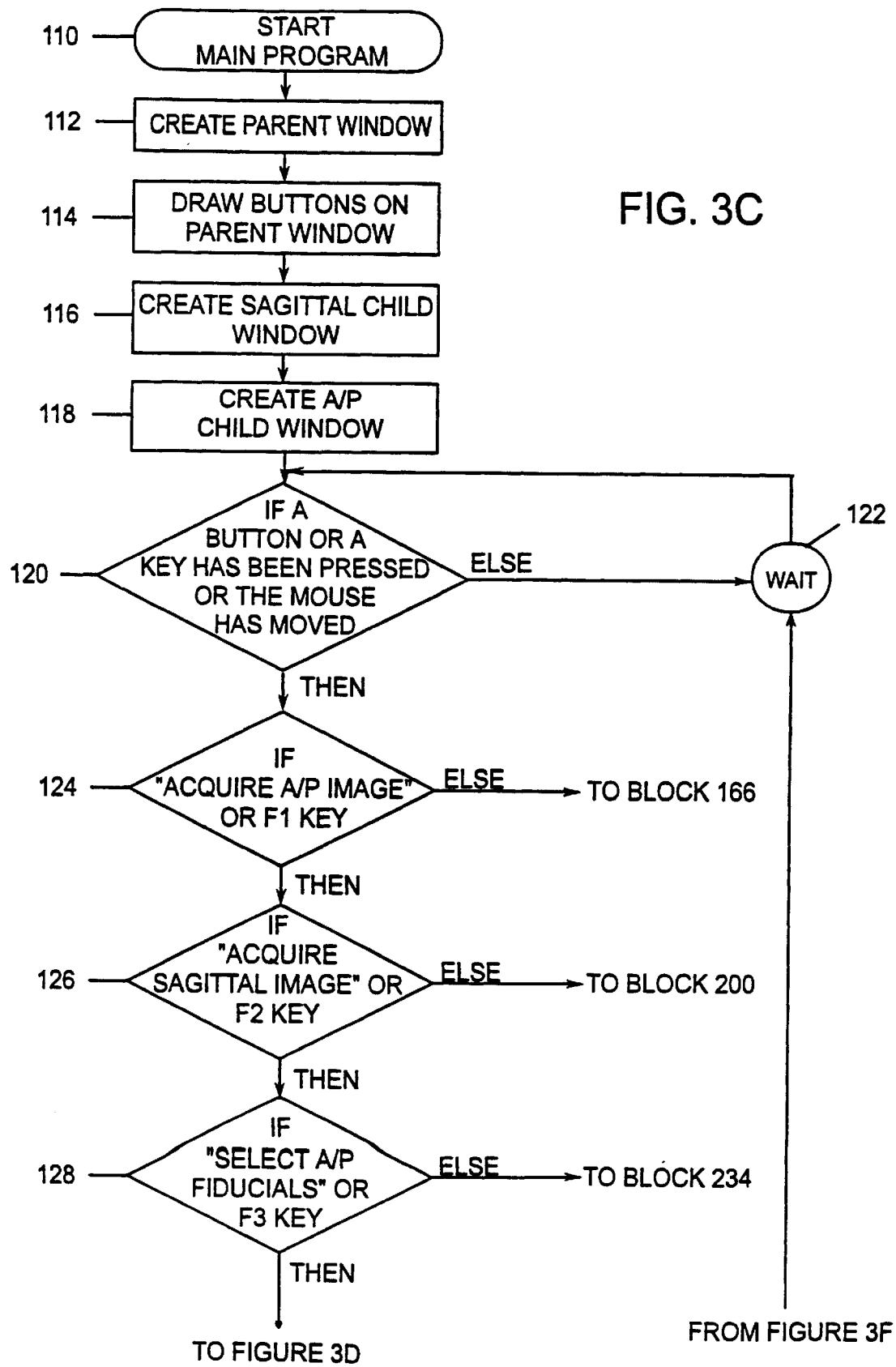

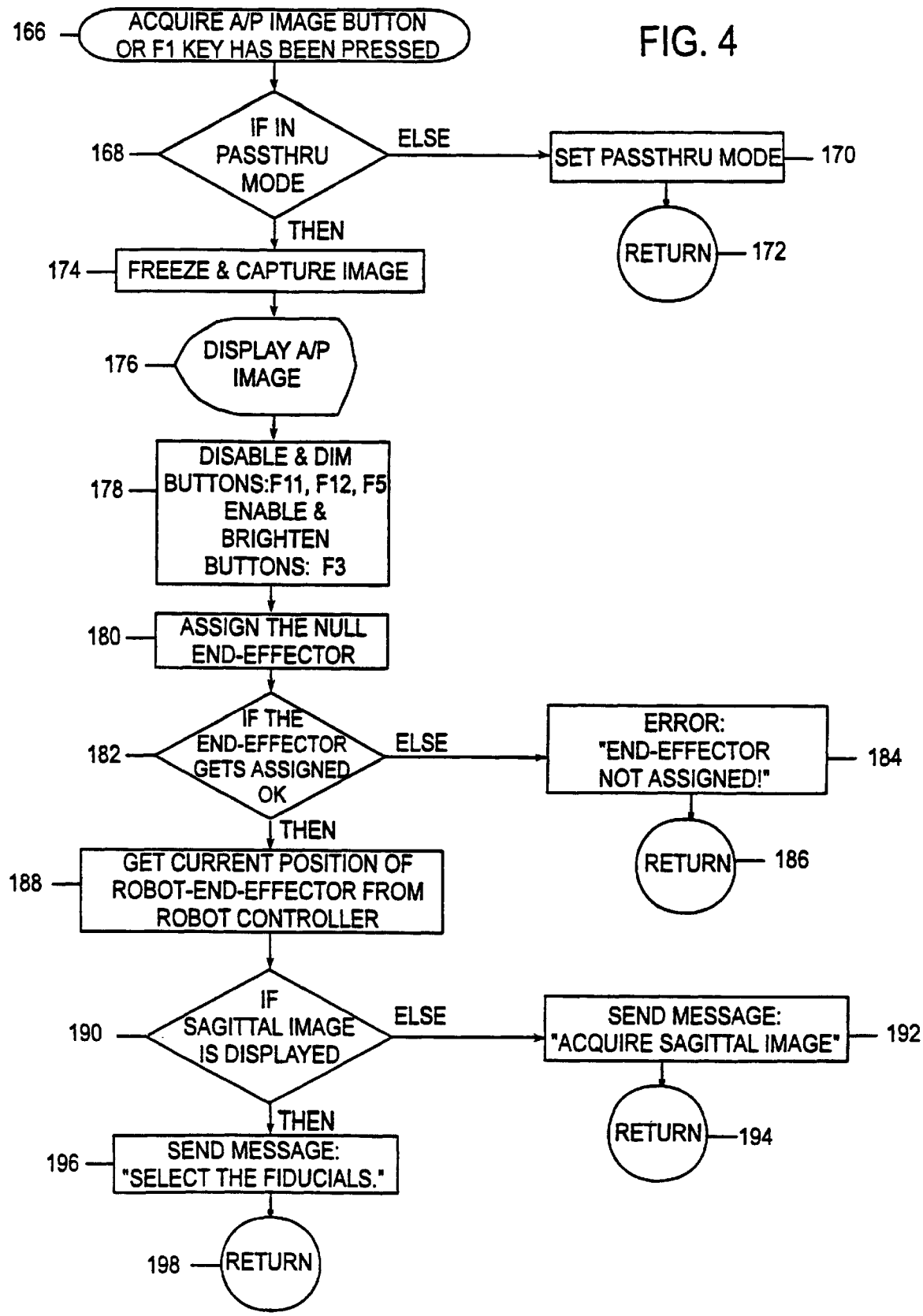

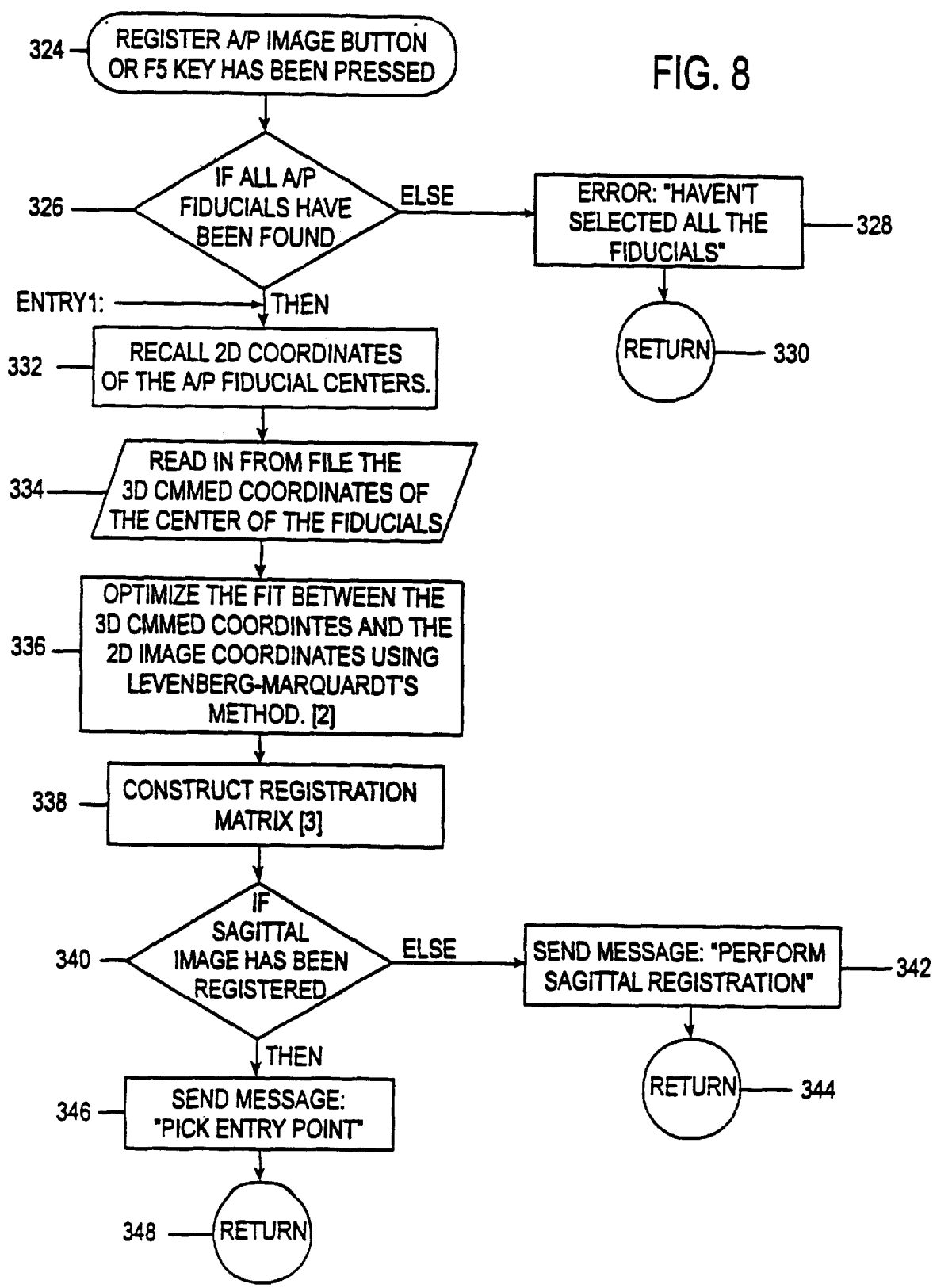

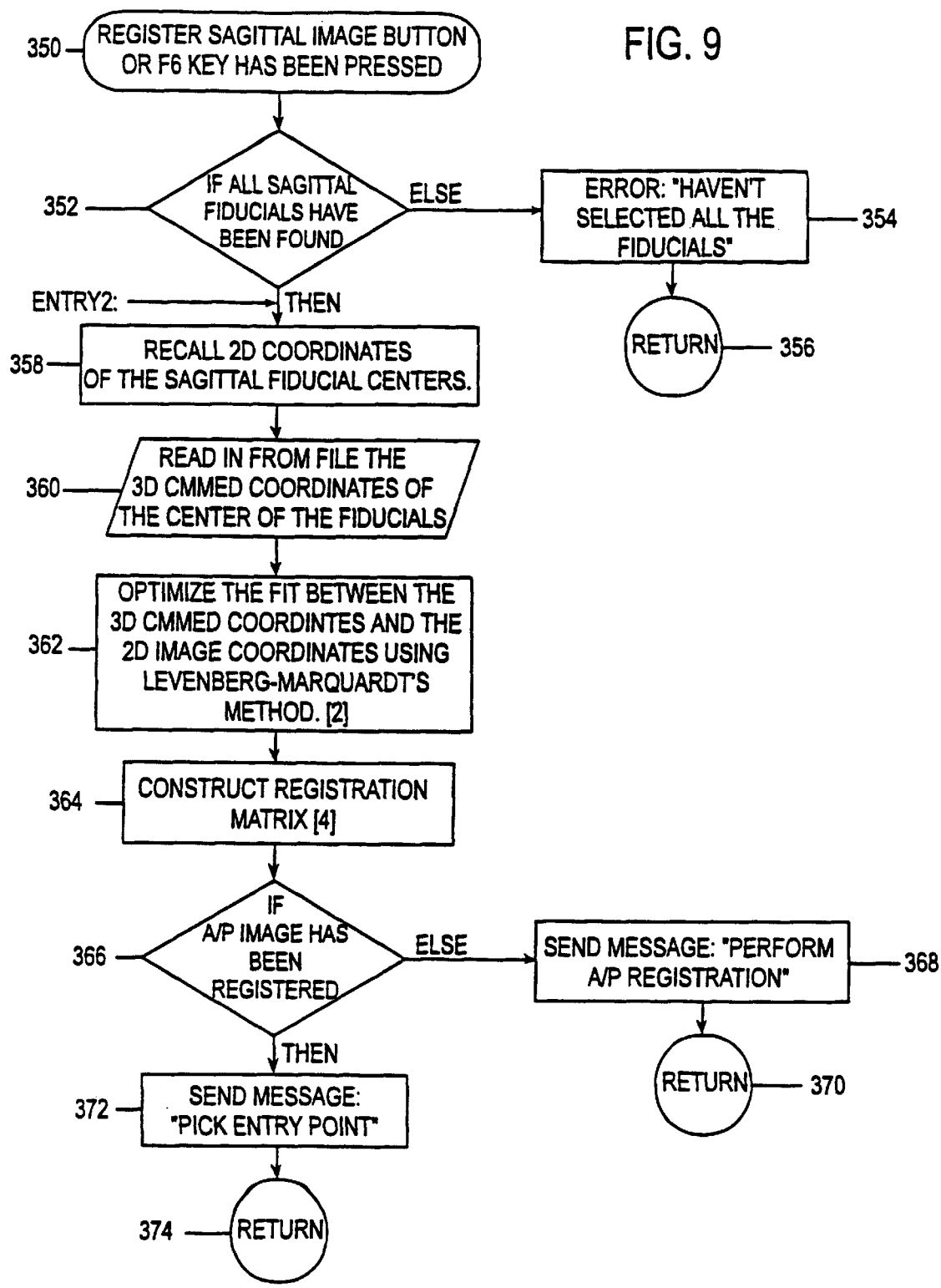

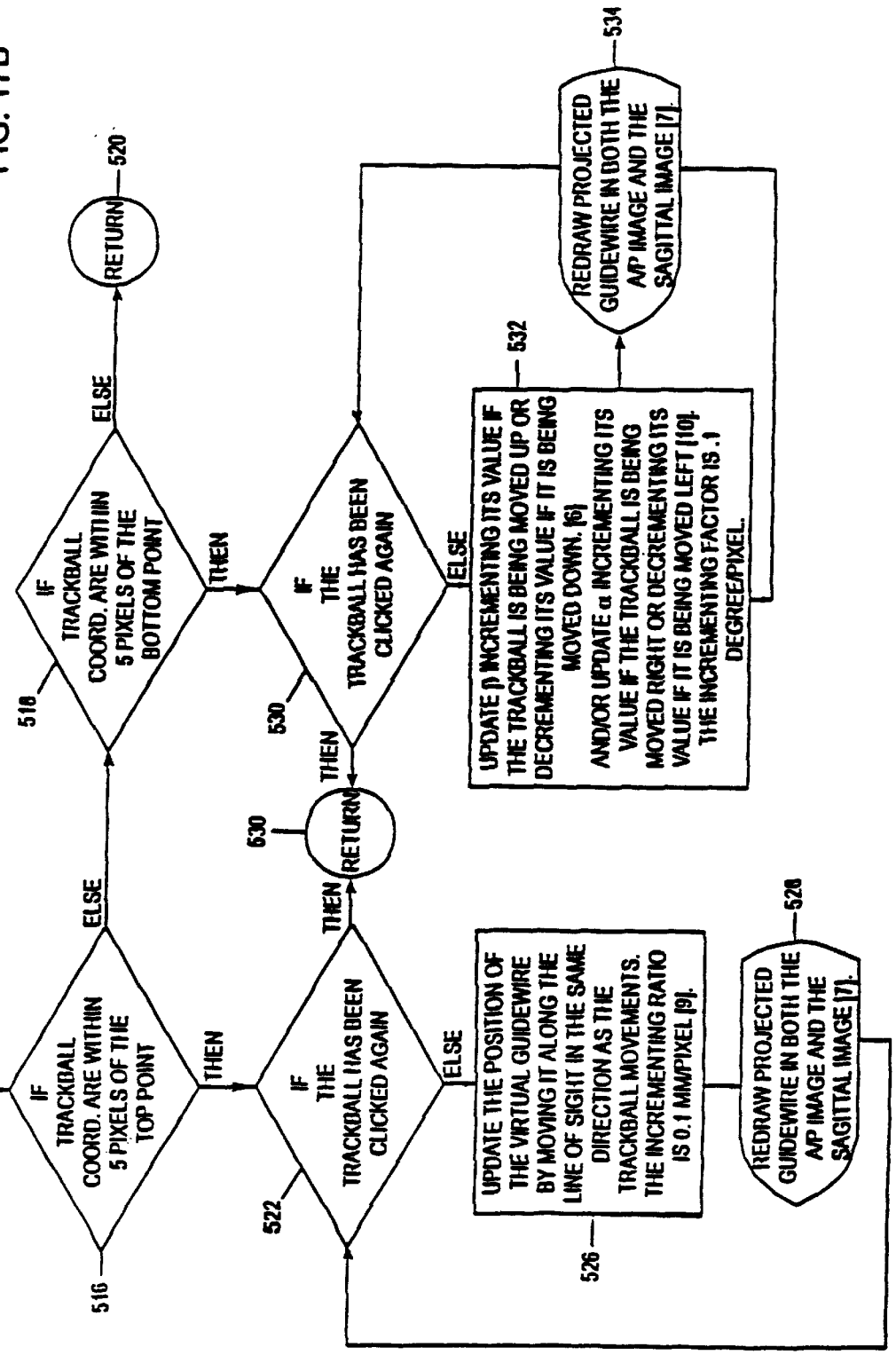

APPARATUS AND METHOD FOR PLANNING A STEREOTACTIC SURGICAL PROCEDURE USING COORDINATED FLUOROSCOPY

This is a continuation of application Ser. No. 09/020,767, filed Feb. 9, 1998, which is a continuation of application Ser. No. 08/649,798 filed May 17, 1996, now U.S. Pat. No. 5,799,055, which in turn is a continuation of application Ser. No. 08/648,313 filed May 15, 1996 now abandoned.

This invention was made with government support under Grant No. DMC-8857854 awarded by the National Science Foundation. The U.S. government has certain rights in the invention.

BACKGROUND AND SUMMARY OF THE INVENTION

The present invention relates to an apparatus and method for planning and guiding insertion of an object along a linear trajectory into a body. More particularly, the present invention relates to an apparatus and method for coordinating two captured fluoroscope images to permit effective three-dimensional planning of the trajectory using only two-dimensional images.

Numerous medical interventions involve placing a needle, drill, screw, nail, wire or other device in the body. In some cases the angle and position of the device are both of critical importance, for example in the drilling of a hole for a screw along the axis of a spinal pedicle. In other cases, it is primarily the positioning of the end-point of the device which is important, for example in placing a biopsy needle into a suspected tumor. In still other cases, the objective is only to define a point rather than a line, for example in targeting a tumor for radiation therapy. Many other examples exist, especially in the field of orthopaedics.

The present invention is also relevant to the development of percutaneous technique. Executing a linear trajectory for the insertion of instrumentation into the body through the skin is more difficult than open surgical technique, but the reduced invasiveness and trauma of percutaneous placement makes it desirable.

Fluoroscopy is frequently used by surgeons to assist medical procedures. Continuous fluoroscopy during a surgical procedure is undesirable because it exposes the surgeon's hands to radiation. Furthermore, regardless of whether intermittent or continuous fluoroscopy is used, the resulting images are two-dimensional while insertion of the surgical instrument requires three-dimensional awareness by the surgeon.

The apparatus and method of the present invention involve acquisition and storage of two separate fluoroscopic images of the body, taken from two different angles. Typically, although not necessarily, these would be an anterior/posterior (A/P) image taken front-to-back of the patient, and a sagittal image taken side-to-side. These two fluoroscopic images are displayed on two adjacent computer monitors. The surgeon uses a trackball or other computer input device to specify on the monitors an insertion point and an insertion trajectory.

A mechanical positioning device is then used to position a guide through which the surgeon performs the insertion of the surgical instrument. The positioning device may either be an active computer controlled manipulator such as a robot, or it may be a manually adjusted mechanical device which is set numerically in accordance with an output from the computer.

The apparatus and method of the present invention establish the projective geometric relationships relating each of two acquired fluoroscopic images to the three-dimensional workspace around and within the patient's body, despite essentially arbitrary positioning of the fluoroscope. The two images then become a coordinated pair, which permits three-dimensional planning that might otherwise be expected to require a computed tomography (CT) scan.

While the acquisition and display of two approximately orthogonal images may be expected to present the surgeon with the greatest ability to plan in three dimensions, two images are not strictly necessary. It is possible to use a single captured image for some procedures, particularly if the surgeon has adjusted the beam axis of the fluoroscope into alignment with the intended trajectory. Furthermore, more than two images could also be acquired and coordinated, should that be advantageous.

Several other approaches to stereotactic or robotic surgery, planned on a computer screen displaying medical images, have been described by other workers, and will be listed below. Some background is given here before discussing prior art. The method and apparatus of the present invention constitute a technique we call coordinated fluoroscopy. Coordinated fluoroscopy is a technique for REGISTRATION and for SURGICAL PLANNING. It allows registration based on the acquired fluoroscopic images themselves, without requiring any additional measuring devices. It allows three-dimensional surgical planning based on fluoroscopic views from two angles, without requiring three-dimensional imaging such as computed tomography (CT), and without requiring that the two fluoroscopic images be acquired from orthogonal fluoroscope poses.

Registration

Registration is a key step in any image-guided surgical system. Registration is the determination of the correspondence between points of the image upon which a surgical plan is prepared, and points of the workspace in the vicinity of (and within) the patient. If a numerically controlled tool (whether robotic or manual) is to be used, the coordinate system of that device must also be brought into registry with the image.

It is common to accomplish registration with the help of a global positioning device, usually optical, which can measure the three-dimensional coordinates of markers placed anywhere over a large volume of space. Coordinated fluoroscopy avoids the necessity for this expensive and inconvenient device, instead deriving registration directly from the acquired fluoroscopic images themselves. Coordinated fluoroscopy uses a "registration artifact" which is held in a fixed position relative to the patient while one or more fluoroscopic images are acquired from different angles (poses). There is no need to constrain the fluoroscope poses at which these various images are acquired, for instance to require that they be orthogonal, nor is there a need to instrument the fluoroscope so that the pose angles can be measured. Instead, pose information is extracted after-the-fact from the images. It is a substantial benefit of the present invention that surgeons can acquire fluoroscopic images using fluoroscope poses of their own choosing, as they are accustomed.

The registration artifact contains a plurality of features (fiducials) which are designed to be easily identifiable on a fluoroscopic image. The embodiment described here uses eight small steel spheres embedded in a radiolucent matrix. The positions of these fiducials are known relative to a coordinate system fixed in the artifact, either by design or by measurement.

From the two-dimensional locations of the projections of these fiducials in a fluoroscopic image, we can determine the geometric projections that carry a general three dimensional point anywhere in the vicinity of the artifact into a projected point on the image. This establishes registration between image and workspace. Several images can each be registered relative to the same registration artifact, thus also bringing all the images into registry with one another.

Identification of the geometric projections, as discussed above, would not be possible with raw fluoroscope images, which are highly nonlinear and distorted. It is necessary first to map and compensate for these distortions. It is useful to be aware of the necessity of distortion compensation when comparing the present invention to prior art.

Surgical Planning

Surgical planning is also a key step in image-guided surgery. Planning of three-dimensional surgical procedures might be expected to be done on a three-dimensional dataset, such as can be reconstructed from computed tomography (CT) data. However, surgeons are accustomed to planning on two-dimensional images: radiographs or fluoroscopic images. Indeed even when CT data is available, planning is usually done on individual two-dimensional CT "slices" rather than on a three-dimensional reconstruction.

The coordinates of the endpoints of a line segment representing an intended screw, biopsy needle, or drilled hole are of course three-dimensional, as are the coordinates of a single point within the body marking the present location of a tumor or a fragment of shrapnel. In surgical planning such points can be specified on a two-dimensional image, or on each of several two-dimensional images. Each such two-dimensional image is a projection of the same three-dimensional space.

It is necessary to convert the two-dimensional coordinates of specified points on each of several images into a three-dimensional coordinate which can be used to guide a tool along a desired trajectory or to a desired point within the body. To do so one must have knowledge of the geometric relationship of the projections that created the images.

In the absence of such geometric knowledge a point specified on one image and a point independently specified on another image may in fact not correspond to any single point within the body. This is so because a point specified on a two-dimensional image is the projection of a LINE in space. The implied point in three-dimensions is the intersection of two such lines, one implied by the point specified on each image. Two such lines created independently may be skew, intersecting nowhere. Similarly, line segments for an intended procedure can not be chosen independently on two images, otherwise they will in general not correspond to a well-defined three-dimensional line segment.

In coordinated fluoroscopy, the geometric projections that relate the two images to a single three-dimensional coordinate system are established before planning commences. The points chosen by the surgeon on two (or more) images can therefore be constrained by the software such that they DO correspond to a well-defined point in three-dimensions. In practice, as a surgeon adjusts an intended point or line segment on one image, the point or line segment displayed on the other image(s) continuously updates and adjusts as well. One cannot draw "arbitrary" points or line segments independently on the images; the software only allows one to draw points or line segments that correspond to a well-defined point or line segment in three-dimensions.

The benefits of planning on geometrically coordinated images as described above are threefold:

1) Once the surgeon has selected a point or a line segment on two images, the three-dimensional point or line segment to which the selections correspond is fully defined and ready to be executed.

2) An axial view such as could be attained from a CT slice is generally unattainable fluoroscopically. The angle that is most easily visualized in axial view, known as the transverse angle, is therefore difficult to select or execute under fluoroscopy. In coordinated fluoroscopy the transverse angle is implicitly specified by the surgeon by selecting line segments on two images. This may assist the surgeon in visualizing and planning the transverse angle for a procedure.

3) In conventional fluoroscopy, image dilation due to beam divergence is of unknown extent, making accurate measurement of anatomic distances difficult. In coordinated fluoroscopy the actual in-situ length of an intended line segment can be determined by the software. This is useful for selecting appropriate screw length, as well as for other purposes.

BACKGROUND

Lavalle et al. in Grenoble, France have developed a system for spinal surgery which uses computed tomography as an image source. The CT data is assembled into a three-dimensional data set which can then be resliced at will on orthogonal planes. Surgical planning proceeds on three mutually orthogonal planes simultaneously. Registration is performed by using an optical tracking device to digitize arbitrary surface points of the vertebrae, and matches those surface points to the CT data set.

Nolte et al. in Bern, Switzerland have developed a very similar spinal system to Lavalle et al. Registration differs in that the optical tracking device is used to digitize specific anatomic landmarks rather than general surface contours. The features are then pointed out manually in CT data, allowing a match to be made.

P. Finlay in High Wycombie, England has developed a fluoroscopic system for head-of-femur (hip) fractures. Accuracy requirements in this procedure are not very great, so fluoroscope distortion compensation is not needed. Its absence also precludes identification of the geometric projections from images as is done in the present invention. Instead, the two fluoroscope poses are required to be orthogonal and the C-arm must not be moved along the floor in between the two images. Registration is accomplished by noting various features of a surgical tool which appears in the images, and by highlighting a marker wire which also appears in the field of view of the fluoroscope.

Potamianos et al. in London, England have developed a system for kidney biopsy and similar soft-tissue procedures. It incorporates a digitizing mechanical arm to which a biopsy needle is attached, and which can be moved about manually by the surgeon. Surgical planning per se is absent; instead a line segment representing the present position of needle is displayed superimposed upon captured (static) fluoroscope images, as the needle is moved manually near and within the patient.

Phillips et al. in Hull, England have developed a system for orthopaedic procedures. It uses a optical tracking device as well as a fluoroscope. Registration is accomplished by instrumenting the fluoroscope with light emitting diodes and tracking them with the optical tracker. surgical planning software is specific to the surgical procedure, and tends to offer medical opinion rather than just display a trajectory as in the present invention. For intramedullary nail placement, for instance, the surgeon outlines target holes in an intramedullary prosthetic, and software calculates a trajectory through them.

U.S. Pat. No. 4,750,487 (Zanetti) describes a stereotactic frame which overlays a patient. A single anterior/posterior fluorograph is then acquired, in which a crosshairs affixed to the frame is visible. By measuring the displacement of the crosshairs from the desired target, a motion of the frame can be accomplished which brings the two into alignment. This invention does not facilitate three-dimensional stereotaxy as does the present invention.

U.S. Pat. No. 5,078,140 (Kwoh) describes a stereotactic and robotic system for neurosurgery. It uses CT images.

ASPECTS OF THE INVENTION

According to the present invention, a method is provided for planning a stereotactic surgical procedure for a linear trajectory insertion of surgical instrumentation into a body using a fluoroscope for generating images of the body. The method includes placing adjacent to the body a registration artifact containing a plurality of fiducials; displaying on a computer monitor an image of the patient's body and the registration artifact; receiving a user or automatic algorithmic input to identify two-dimensional coordinates of the fiducials of the registration artifact displayed on the first monitor; and registering the image by creating a geometric model having parameters, said model projecting three-dimensional coordinates into image points, and numerically optimizing the parameters of the geometric model such that the projections of the known three-dimensional coordinates of the fiducials best fit the identified two-dimensional coordinates in the image.

The method further includes displaying on a second computer monitor a second image, taken of the patient's body and the registration artifact but from an angle different from that of the first image, and receiving a user or automatic algorithmic input to identify two-dimensional coordinates of the fiducials displayed on the second computer monitor; and registering the second image by creating a geometric model having parameters, said model projecting three-dimensional coordinates into image points, and numerically optimizing the parameters of the geometric model such that the projections of the known three-dimensional coordinates of the fiducials best fit the identified two-dimensional coordinates in the second image.

The method, whether one or two images have been acquired, further includes the step of receiving a user input to select on a computer monitor an entry point for a surgical instrument. In the case of two images, also receiving a user input to select on a computer monitor the position, length, and angles of a virtual guidewire representing the trajectory for the surgical instrument; and drawing a segment, to be known as a PROJECTED GUIDEWIRE, on the image(s). When there are two images, the projected guidewires are constrained to correspond geometrically to the same three-dimensional segment in space, to be known as the VIRTUAL GUIDEWIRE.

The method further includes receiving a user input to move either end of a projected guidewire, by revising the virtual guidewire of which the projected guidewire(s) are projections, and by redrawing the projected guidewires in correspondence with the revised virtual guidewire.

The method further includes receiving a user input to change the length of the virtual guidewire, and redrawing the projected guidewire(s) in correspondence with the revised virtual guidewire. A special case is that the length is zero, so that what is planned is a virtual targetpoint rather than a virtual guidewire.

The method further includes receiving a user input to change the sagittal, transverse, or coronal angle(s) of the virtual guidewire, updating the orientation of the virtual guidewire based on the new angles, and redrawing the projected guidewire(s) in correspondence with the revised virtual guidewire.

The method further includes producing an output to adjust the coordinates of a tool guide such that the projection of the axis of the guide in an image is brought into correspondence with the entry point displayed on the computer monitor.

The method further includes producing an output to adjust the coordinates of a tool guide such that it is brought into correspondence with the virtual guidewire; or producing an output to adjust the coordinates of a tool guide such that the position of the guide along its axis is offset by a preselected distance from one endpoint of the virtual guidewire, in order to control the location within the body of the surgical instrument to be inserted.

The method further includes transmitting said coordinates to a robot or other automatic mechanical device, or displaying said coordinates such that human operator may manually adjust a mechanical device.

BRIEF DESCRIPTION OF THE DRAWINGS

The detailed description particularly refers to the accompanying figures in which:

FIGS. 3C, 3D, 3E, and 3F are flow charts of the steps performed by the computer during a main program loop;

FIGS. 4 is a flow chart illustrating the steps performed by the computer to acquire an A/P image from the fluoroscope;

FIGS. 6A and 6B are flow charts illustrating the steps performed by the computer and the user to select or identify A/P fiducials from the A/P image displayed in FIG. 3a;

FIG. 8 is a flow chart illustrating the steps performed by the computer to register the A/P image;

FIG. 9 is a flow chart illustrating the steps performed by the computer to register the sagittal image;

FIGS. 16A and 16B are flow charts illustrating the steps performed by the computer when the computer receives a user input based on a cursor in the A/P image area of FIG. 3a;

FIGS. 17A and 17B are flow charts illustrating the steps performed by the computer when the computer receives a user input based on a cursor in the sagittal image area in FIG. 3b.

DETAILED DESCRIPTION OF THE DRAWINGS

Figures 1, 2:
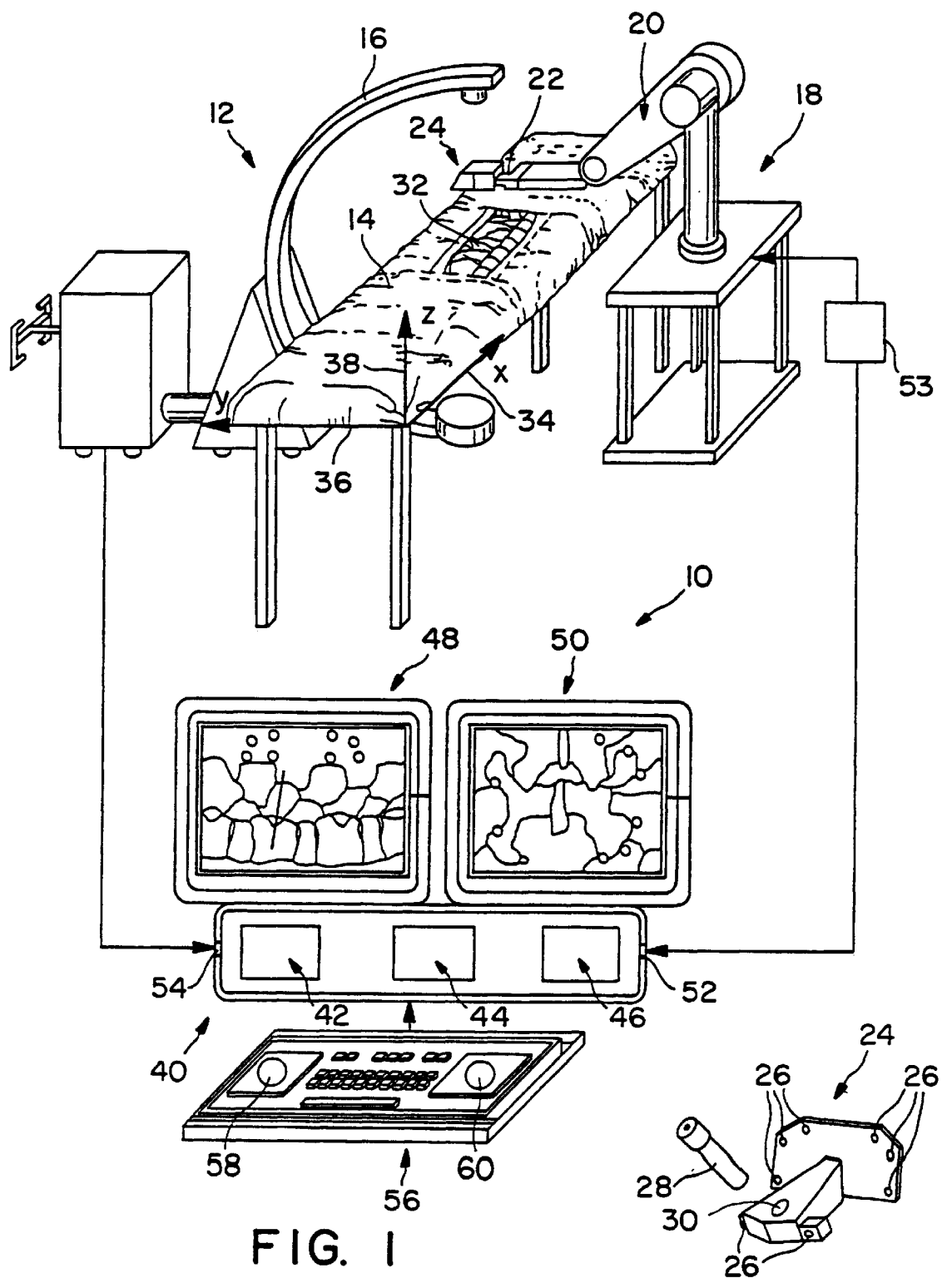
FIG. 1 is a diagrammatic illustration of the stereotactic surgical apparatus of the present invention for coordinating images from a fluoroscope, planning a linear trajectory medical intervention, and controlling a robot to control the linear trajectory medical intervention.
FIG. 2 is a perspective view of a registration artifact and tool guide of the present invention.

Referring now to the drawings, FIG. 1 illustrates the stereotactic system 10 for linear trajectory medical interventions using calibrated and coordinated fluoroscopy. The apparatus and method of the present invention is A designed to utilize images from a fluoroscope 12 such as a standard C-arm which generates fluoroscopic or x-ray images of a body on a surgical table 14. The imaging arm 16 is moveable so that both anterior/posterior (A/P) and sagittal or side images of the body can be taken.

A robot 18 is situated adjacent the surgical table 14. Illustratively, the robot is a PUMA-560 robot. The robot 18 includes a movable arm assembly 20 having an end flange 22. An alignment or registration artifact 24 is coupled to the end flange 22 of robot 18.

The registration artifact 24 is best illustrated in FIG. 2. The artifact 24 is X-ray and visually transparent with the exception of 8 opaque spheres or fiducials 26, and an aperture 30 to hold a tool guide 28 through the artifact 24. Initially, the artifact 24 is positioned roughly over the area of interest of body 32 and within the field of view of the fluoroscope 16. Therefore, the fiducials 26 show up as distinct dots on the A/P and sagittal images as discussed below. The shape of the artifact is designed so that the image dots from the fiducials 26 will not over shadow each other and is sensitive to any angular deviations. The robot arm 20 can adjust the artifact 24 in three-dimensions about X-axis 34, Y-axis 36, or Z-axis 38 illustrated in FIG. 1.

The coordinated fluoroscopic control system of the present invention is controlled by computer 40, which includes a microprocessor 42, and internal RAM 44, and a hard disk drive 46. Computer 40 is coupled to two separate graphics monitors 48 and 50. The first graphics monitor 48 displays a sagittal image taken by the C-arm 12. The second monitor 50 displays an A/P image taken by the C-arm 12. Computer 40 further includes a serial communication port 52 which is coupled to a controller 53 of robot 18. Computer 40 is also coupled to C-arm 12 for receiving the images from the C-arm 12 through an image acquisition card 54. Computer 40 is also coupled to an input device 56 which is illustratively a keyboard having a track ball input control 58. Track ball input 58 controls a cursor on both monitor 48, 50.

Figure 3A:
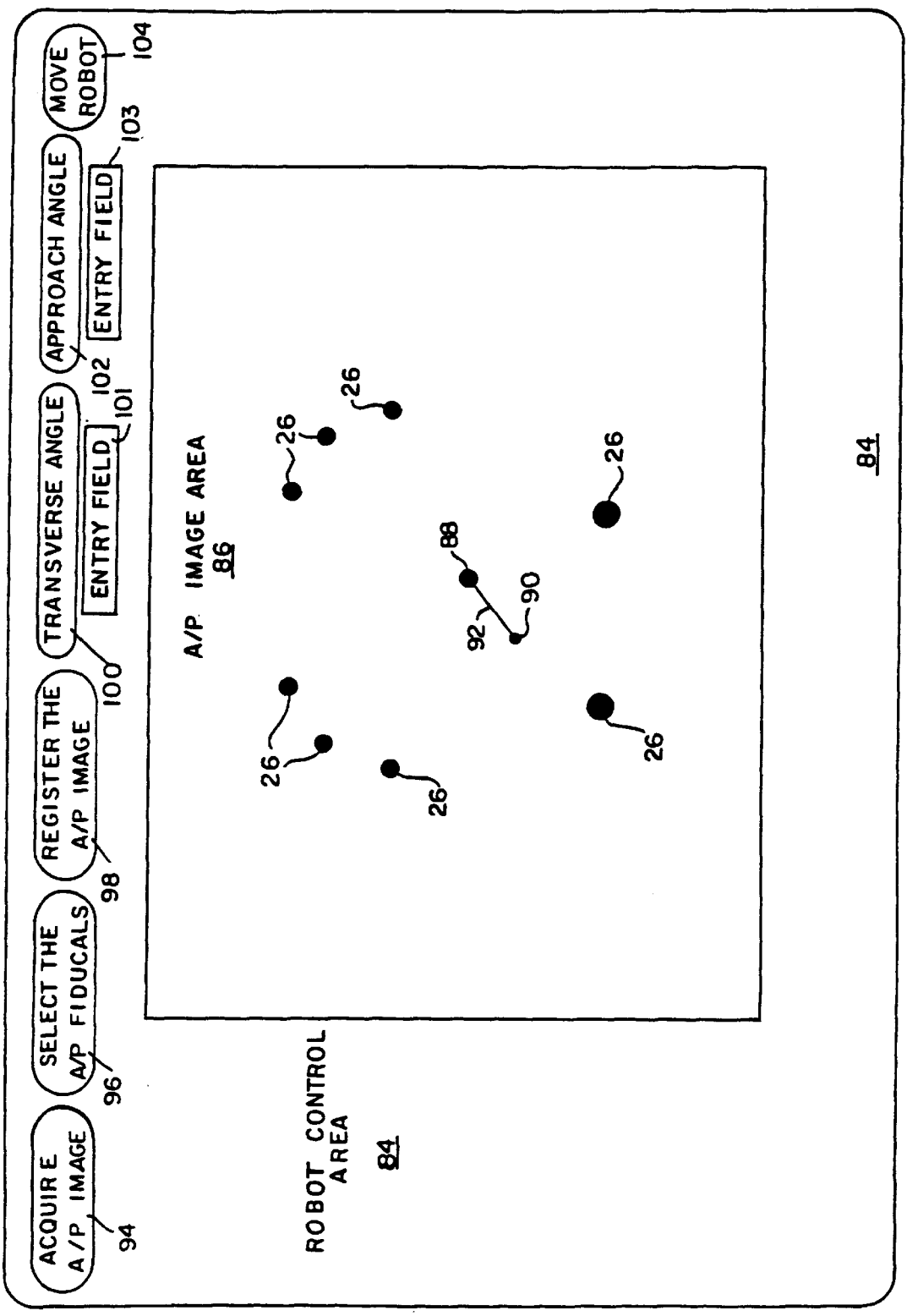
FIG. 3a is a sample screen display of the user interface which includes an anterior/posterior (A/P) taken by the fluoroscope and displayed on a first computer monitor along with a number of the buttons and entry fields necessary to run the program.
Figure 3B:
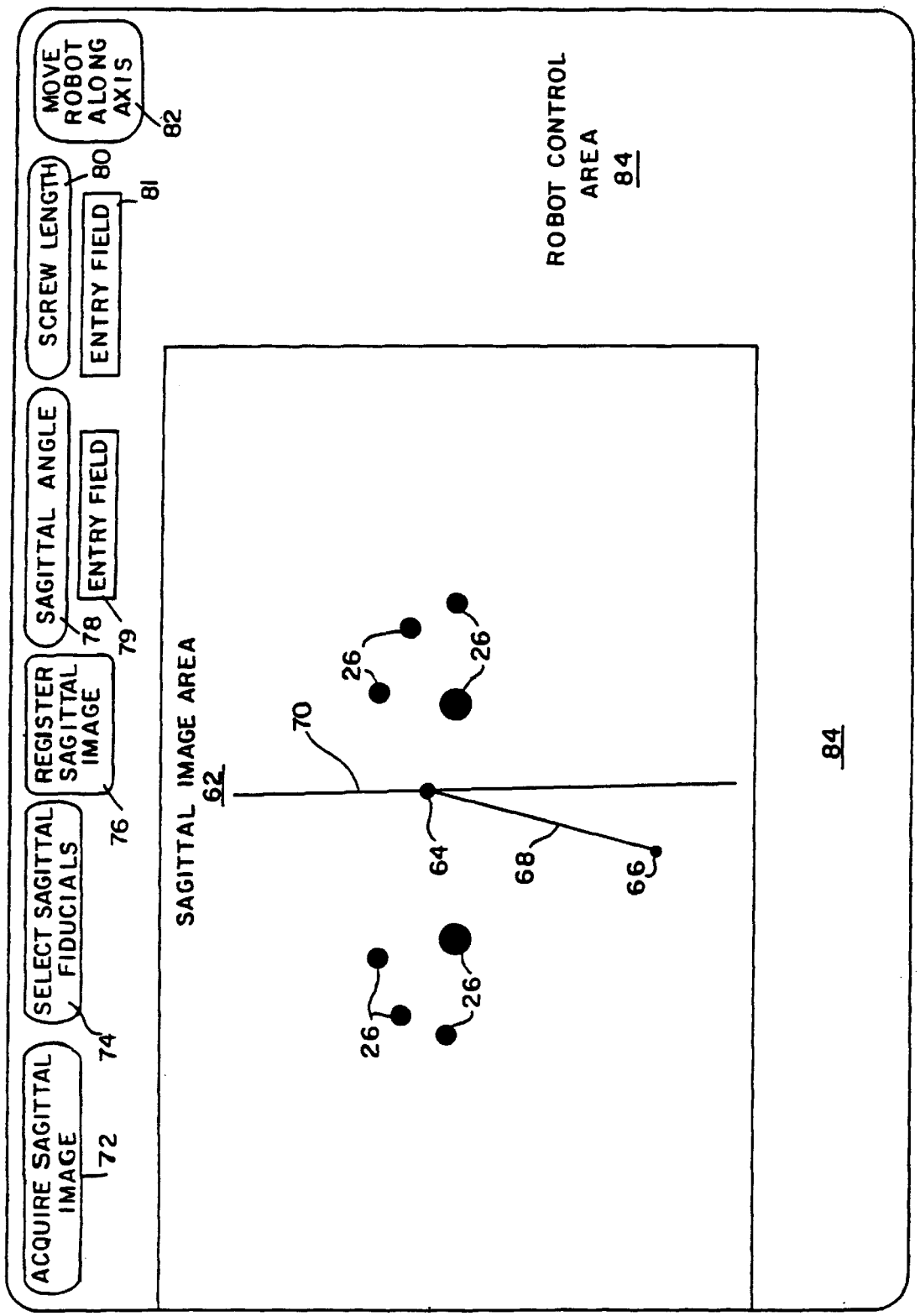
FIG. 3b is a sample screen display which includes a sagittal image taken by the fluoroscope and displayed on a second computer monitor along with a number of the buttons and entry fields necessary to run the program.
Figure 3D:
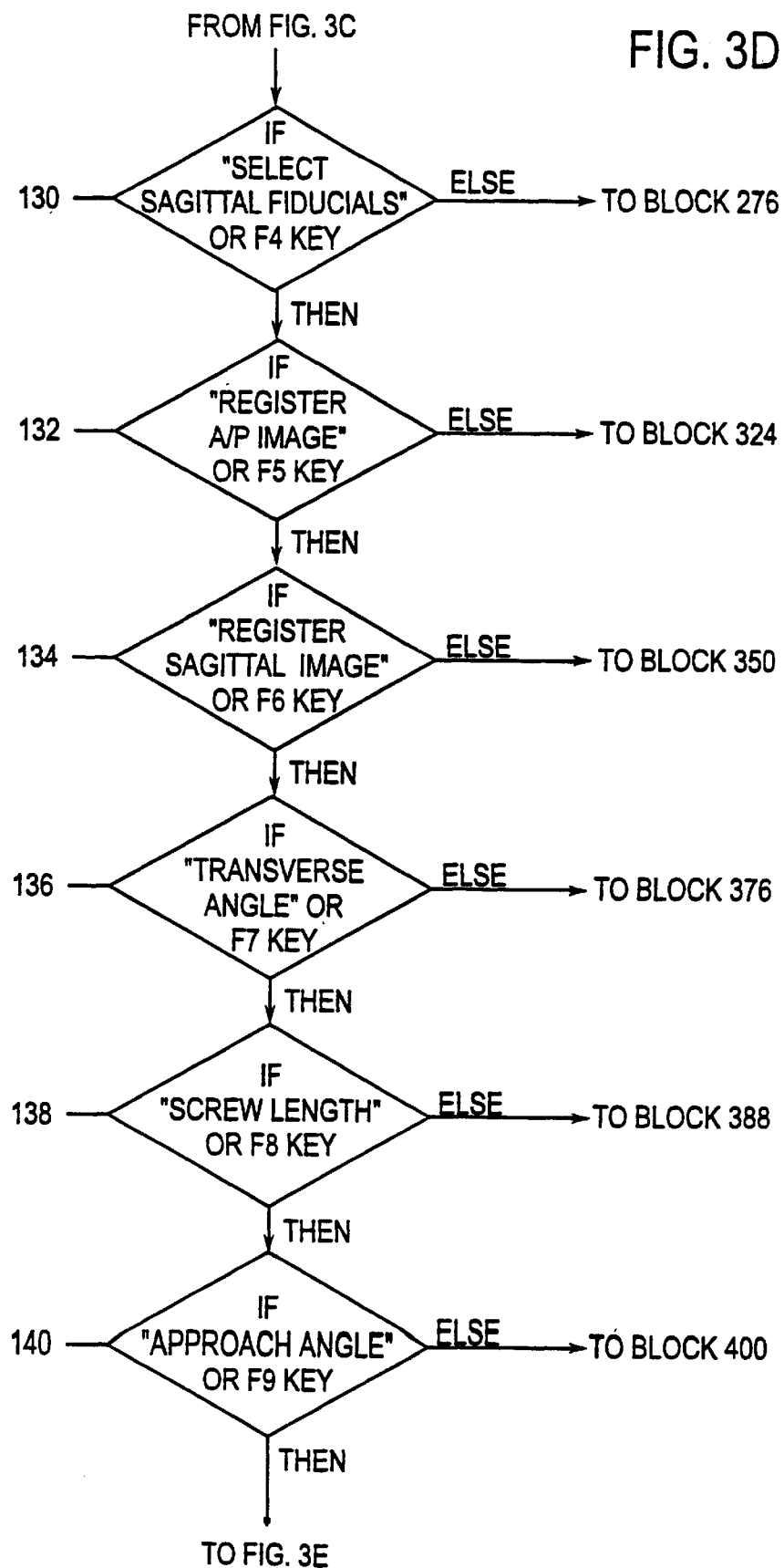
Figure 3E:
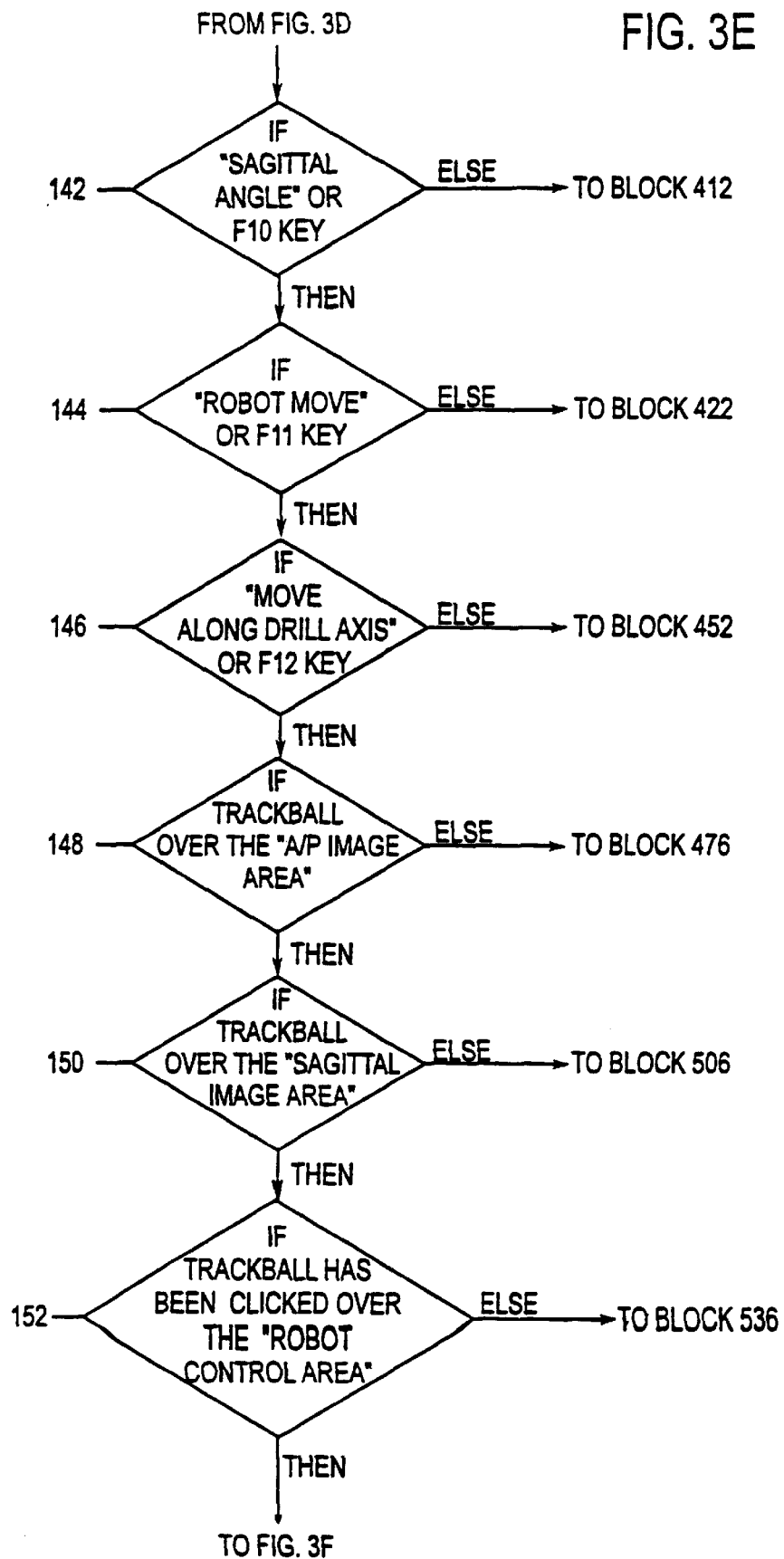
Figure 3F:
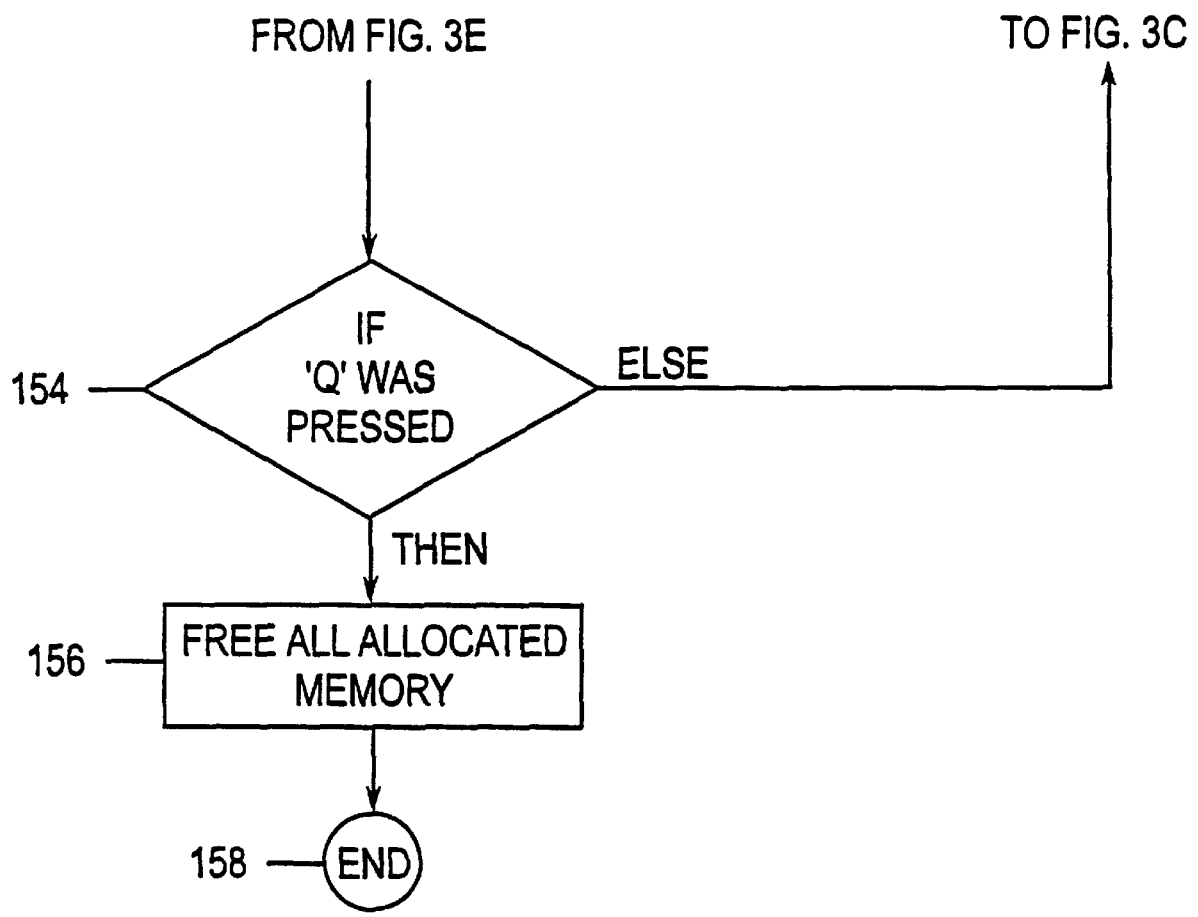

The displays on monitors 48 and 50 are illustrated in FIGS. 3a and 3b. Referring now to FIG. 3b, the sagittal image is displayed in area 62 on monitor 48. All eight fiducials 26 should appear in the sagittal image area 62. If not, the artifact 24 or the C-arm 12 should be adjusted. As discussed in detailed below, computer 40 displays a top entry point 64 and a bottom point 66 of a projected guidewire 68. The projected guidewire 68 is a line segment which is displayed on the sagittal image area representing the position of the instrumentation to be inserted during the stereotactic surgical procedure. A line of sight 70 is also displayed in the sagittal image area 62.

Various user option buttons are displayed on monitor 48. The surgeon or operator can access these options by moving the cursor to the buttons and clicking or by selecting the appropriate function keys (F1, F2, etc.) on the keyboard. The option buttons displayed on monitor 48 include button 72 (function F2) for acquiring the sagittal image, button 74 (F4) for selecting sagittal fiducials, and button 76 (F6) for registering the sagittal image. In addition, button 78 (F10) is provided for setting the sagittal angle, button 80 (F8) is provided for setting the screw length, and button 82 (F12) is provided for moving the robot along an axis of the tool guide. Finally, the display screen includes a robot control area 84. The operator can move the cursor and click in the robot control area 84 to control robot 18 as discussed below.

Referring to FIG. 3a, the A/P image displayed on the display screen of monitor 50 is illustrated. The A/P image is displayed in area 86 of the screen. Again, all eight fiducials 26 should appear within the A/P image area 86. The top insertion point of the virtual guidewire is illustrated at location 88, and the bottom point is located at location 90. The projection of the guidewire onto the A/P image is illustrated by line segment 92.

Computer 40 also displays various option buttons on monitor 50. Button 94 (F1) is provided for acquiring the A/P image. Button 96 (F3) is provided for selecting the A/P fiducials. Button 98 (F5) is provided for registering the AP image. Button 100 (F7) is provided for setting a transverse angle of the virtual guidewire, and button 102 (F9) is provided for setting an approach angle for the robot. Button 104 (F11) is provided for moving the robot. Computer 40 also displays a robot control area 84. The operator can move the cursor and click in the robot control area 84 to control robot 18 as discussed in detail below.

The present invention allows the surgeon to select the point of entry for the surgical instrument by moving the top point of the projected guidewire 88 in the A/P image area 86. The operator can also adjust the bottom point of the projected guidewire 90 to specify the transverse and sagittal angle. In addition, the operator can adjust the top point of the projected guidewire 64 to specify the position on the line of sight and bottom point of the projected guidewire 66 to specify the sagittal and transverse angle in the sagittal image area 62. Therefore, the surgeon can select the desired position and orientation of the surgical instrument into the body.

The computer 40 is programmed with software to correct spatial distortions from the optics of the fluoroscope 12. The system of the present invention permits effective three-dimensional planning of the stereotactic surgical procedure using only a pair of two-dimensional fluorographic images displayed on the adjacent monitors 48 and 50. It is not required to use a CT slice in order to fully specify the location of the surgical instrument. The computer 40 establishes the direct geometric relationship between the A/P and sagittal images, despite image distortions and the essentially random or free-hand positioning of the C-arm 12, to establish the A/P and sagittal images. The improved system of the present invention can establish this exact geometric relationship within sub-millimeter accuracy.

Once the sagittal and A/P images are registered, points or lines chosen by the surgeon on one of the A/P image or the sagittal image are immediately displayed by computer 40 as corresponding projections on the other image. Therefore, using the sagittal image on monitor 48 and the A/P image on monitor 50, the surgeon can stereotactically plan the linear trajectory without the requirement of CT scan slice. Accordingly, the procedure of the present invention can be performed without the very expensive CT scan devices which can cost in excess of $1 million.

Details of the operation of the software for controlling the system of the present invention are illustrated in FIGS. 3C–18B.

All of the notations, subscripts and mathematical formulae, equations, and explanations are included in the attached Appendix. Throughout the flow charts described FIGS. 4–18B, reference will be made to the Appendix and to the numbered Sections [1] through [15] set forth in the Appendix.

The main program begins at block 110 of FIG. 3c. Computer 40 creates a parent window at block 112 and then draws buttons on a main window as illustrated at block 114. Computer 40 then creates a sagittal child window on monitor 48 as illustrated at block 116. Computer 40 also creates an A/P child window on monitor 50 as illustrated at block 118. Computer 40 then determines whether a button or key has been pressed at block 120. If not, computer 20 waits as illustrated at block 122 and then returns to block 120 to wait for a button or key to be pressed.

If a button or key was pressed at block 120, computer 40 determines whether the Acquire A/P Image button 94 or the F1 key was pressed at block 124. If so, computer 40 advances to block 166 of FIG. 4. If not, computer 40 determines whether the Acquire Sagittal Image button 94 or the F2 key was pressed at block 126. If so, the computer 40 advances to block 200 of FIG. 5A. If not, computer 40 determines whether the Select A/P Fiducial button 96 or the F3 key was pressed at block 128. If so, computer 40 advances to block 234 of FIG. 6A. If button 96 or the F3 key was not pressed at block 128, computer 40 determines whether the Select Sagittal Fiducial button 74 or the F4 key was selected as illustrated at block 130. If so, computer 40 advances to block 276 of FIG. 7A. If not, computer 40 advances to block 132.

In block 132, computer 40 determines whether the Register A/P Image button 98 or the F5 key was pressed. If so, computer 40 advances to block 324 of FIG. 8. if not, computer 40 determines whether the Register Sagittal Image button 76 or the F6 was pressed as illustrated at block 134. If so, computer 40 advances to block 350 of FIG. 9. If not, computer 40 advances to block 136.

From block 136, computer 40 determines whether the Transverse Angle button 100 or the F7 key was pressed as illustrated at block 138. If so, computer 40 advances to block 376 of FIG. 10. If not, computer 40 determines whether the screw Length button 80 or F8 key was pressed as illustrated at block 140. If so, computer 40 advances to block 388 of FIG. 11. If not, computer 40 determines whether the Sagittal Angle button 78 or the F10 key was pressed as illustrated at block 142. If so, computer 40 advances to block 400 of FIG. 12. If not, computer 40 determines whether the Approach Angle button 102 or the F9 key was pressed as illustrated at block 144. If so, computer 40 advances to block 412 of FIG. 13. If not, computer 40 advances to block 146.

In block 146, computer 40 determines whether the Move Robot button 104 or the F11 key was pressed. If so, computer 40 advances to block 422 of FIG. 14. If not, computer 40 determines whether the Move Robot Along Axis button 82 or the F12 key was pressed as illustrated at block 148. If so, computer 40 advances to block 452 of FIG. 15. If not, computer 40 determines whether the A/P Image area of monitor 50 has been selected by clicking when the cursor is in the A/P image area 86 as illustrated at block 150. If so, computer 40 advances to block 476 of FIG. 16A. If not, computer 40 then determines whether the Sagittal Image area was selected by positioning the cursor in the sagittal image area 62 on monitor 48 and clicking. If so, computer 40 advances to block 506 of FIG. 17A. if not, computer 40 advances to block 154.

From block 154, computer 40 determines whether the robot control area 54 or 106 was selected by moving the cursor and clicking in the Robot Control area 84 on monitor 48 or the Robot Control area 106 on monitor 50. If the Robot Control was selected, computer 40 advances block 536 of FIG. 18A. If the Robot Control was not selected, computer 40 advances to block 158 to determine whether the "Q" key was pressed indicating the operator desires to quit the main program. If the "Q" button was pressed, then computer 40 frees all allocated memory as illustrated at block 160 and ends the main program as illustrated at block 162. If the "Q" button was not pressed at block 158, computer 40 advances back to block 122, waiting for a another button or key to be pressed.

The various functions performed by the system of the present invention will be described in detail. If the Acquire A/P Image button 94 or the F1 key is pressed the, computer 40 advances to block 166 of FIG. 4. Computer 40 then determines whether the image acquisition card is in a passthrough mode at block 168. Button 94 and the F1 key are toggle buttons. When the button 94 or the F1 key is initially pressed, the card is in passthrough mode and images from the C-arm 12 are transmitted directly to the monitor 50. Whatever image is being taken by the C-arm is seen on the monitor 50 in the A/P image area 86. Therefore, if the card is not in the pass-through mode at block 168, pressing button 94 or the F1 key sets the pass-through mode at block 170. Computer 40 then returns to wait for the next command as illustrated at block 172. When the button 94 or the F1 key is pressed again after the image acquisition card within the computer 40 is in pass-through mode, it freezes the live image and captures the A/P image as illustrated at block 174. This captured image is then displayed on monitor 50 as illustrated at block 176. Computer 40 then disables and dims buttons F11, F12 and F5, and enables and brightens button 96 and key F3 as illustrated at block 178. In other words, after the A/P image has been captured, computer 40 allows the operator to have the option to select the A/P fiducials through button 96 or key F3.

Computer 40 then assigns a NULL tool as illustrated at block 180. The NULL tool of the robot is the three-dimensional location of end flange 22 of robot 18. In other words, the end flange 22 establishes a three-dimensional position for the robot, without depending on the particular surgical instrumentation which may be attached to the end flange 22. Computer 40 determines whether the NULL tool was properly assigned at block 182. If not, computer 40 generates an error message "Tool Not Assigned!" as illustrated at block 184. Computer 40 then waits for the next command as illustrated at block 186. If the NULL tool is assigned properly at block 182, computer 40 gets the current position of the end flange from the robot controller 53 as illustrated at block 188. Computer 40 then determines whether the sagittal image is displayed on monitor 48 as illustrated at block 190. If not, computer 40 sends a message of "Acquire Sagittal Image" as illustrated at block 192, and then returns to wait for the next command at block 194. If the sagittal image is displayed at block 190, computer 40 sends the message "Select the Fiducials" as illustrated at block 196. Computer 40 then returns to wait for the next command at block 198.

Figure 5A:
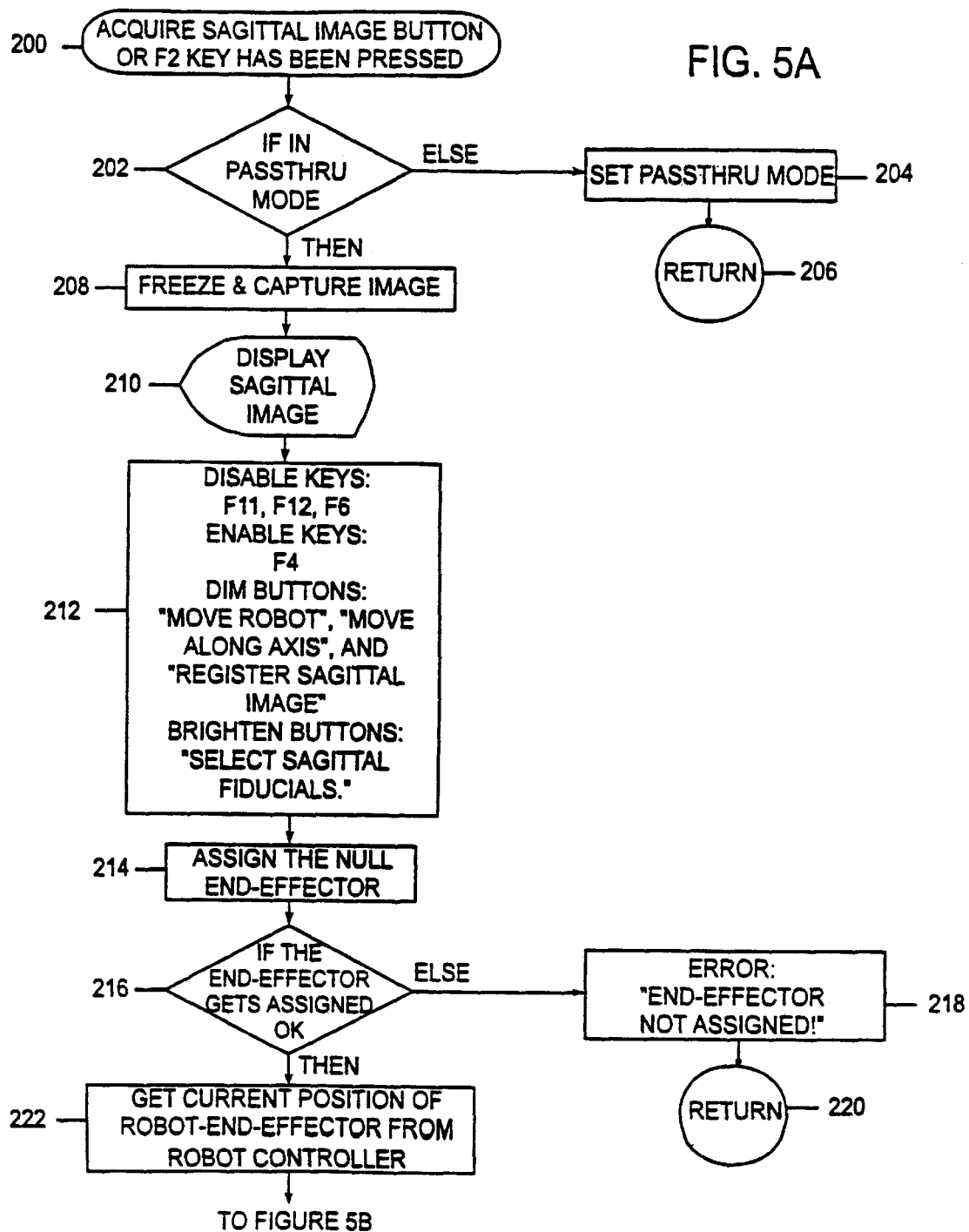
FIGS. 5A and 5B are flow charts illustrating the steps performed by the computer to acquire a sagittal image from the fluoroscope.
Figure 5B:
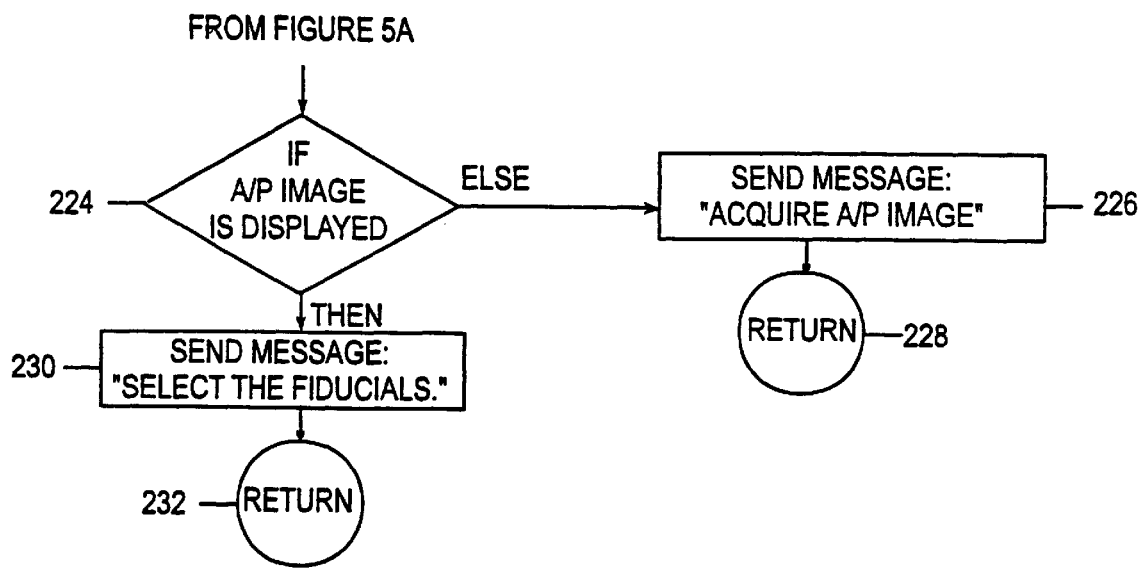

If the Acquire Sagittal Image button 72 or the F2 key is pressed, computer 40 advances to block 200 of FIG. 5A. Computer 40 then determines whether the image acquisition card is in a pass-through mode at block 202. Button 72 and the F2 key are toggle buttons. If the card is not in the pass-through mode at block 202, pressing button 72 or the F2 key sets the pass-through mode at block 204. Computer 40 then returns to wait for the next command as illustrated at block 206. When the button 72 or the F2 key is pressed again after the image acquisition card within the computer 40 is in pass-through mode, it freezes the live image and captures the sagittal image as illustrated at block 208. This captured image is then displayed on monitor 48 as illustrated at block 210. Computer 40 then disables and dims buttons F11, F12 and F6, and enables and brightens button 74 and key F3 as illustrated at block 212. In other words, after the sagittal image has been captured, computer 40 allows the operator to have the option to select the sagittal fiducials through button 74 or key F4.

Computer 40 then assigns a NULL tool as illustrated at block 214. Computer 40 determines whether the NULL tool was properly assigned at block 216. If not, computer 40 generates an error message "Tool Not Assigned!" as illustrated at block 218. Computer 40 then waits for the next command as illustrated at block 220. If the NULL tool is assigned properly at block 216, computer 40 gets the current position of the end flange 22 from the robot controller 53 as illustrated at block 222. Computer 40 then determines whether the A/P image is displayed on monitor 50 as illustrated at block 224. If not, computer 40 sends a message of "Acquire A/P Image" as illustrated at block 226, and then returns to wait for the next command at block 228. If the A/P image is displayed at block 224, computer 40 sends the message "Select the Fiducials" as illustrated at block 230. Computer 40 then returns to wait for the next command at block 232.

Figure 6A:
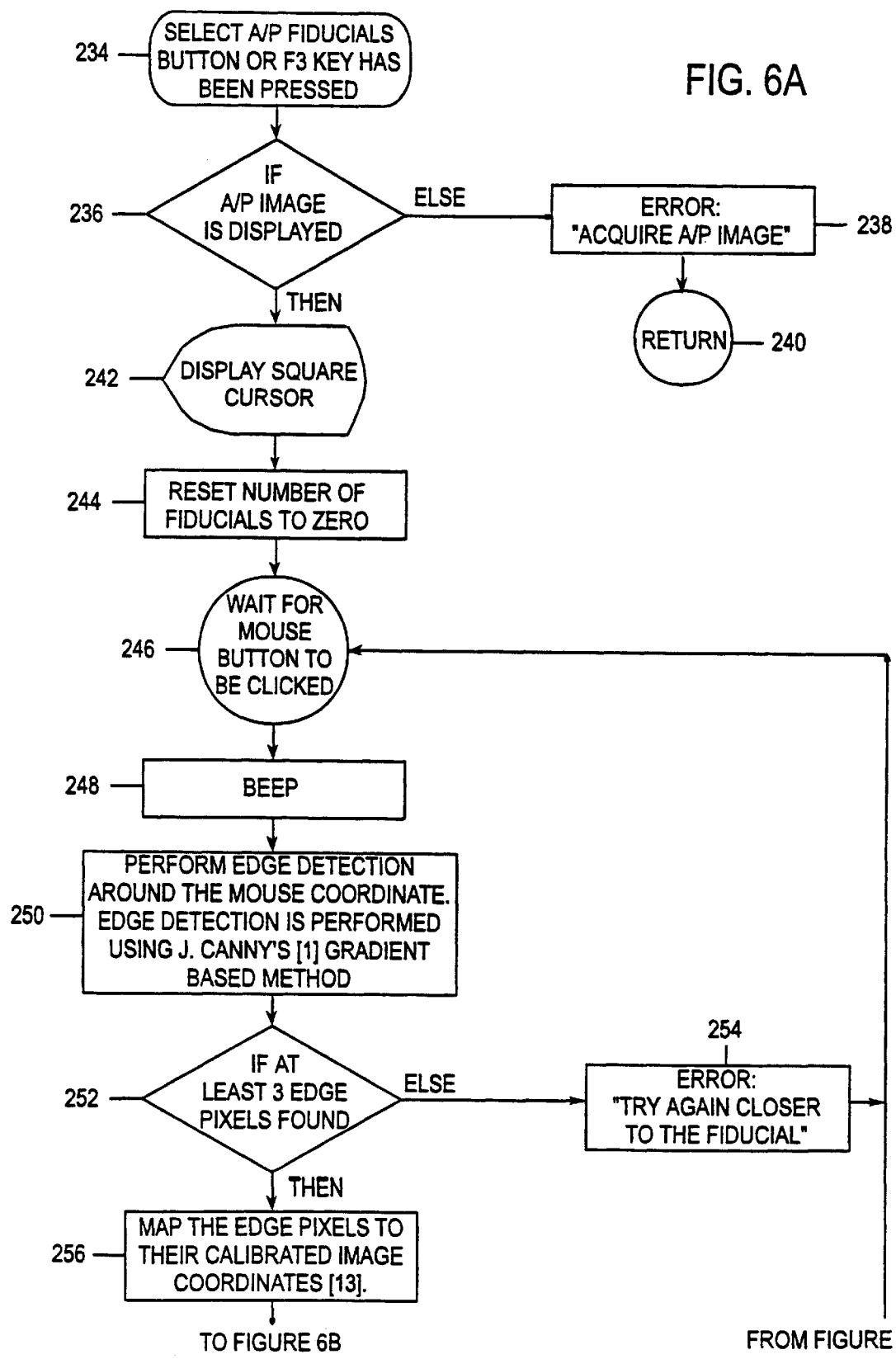
Figure 6B:
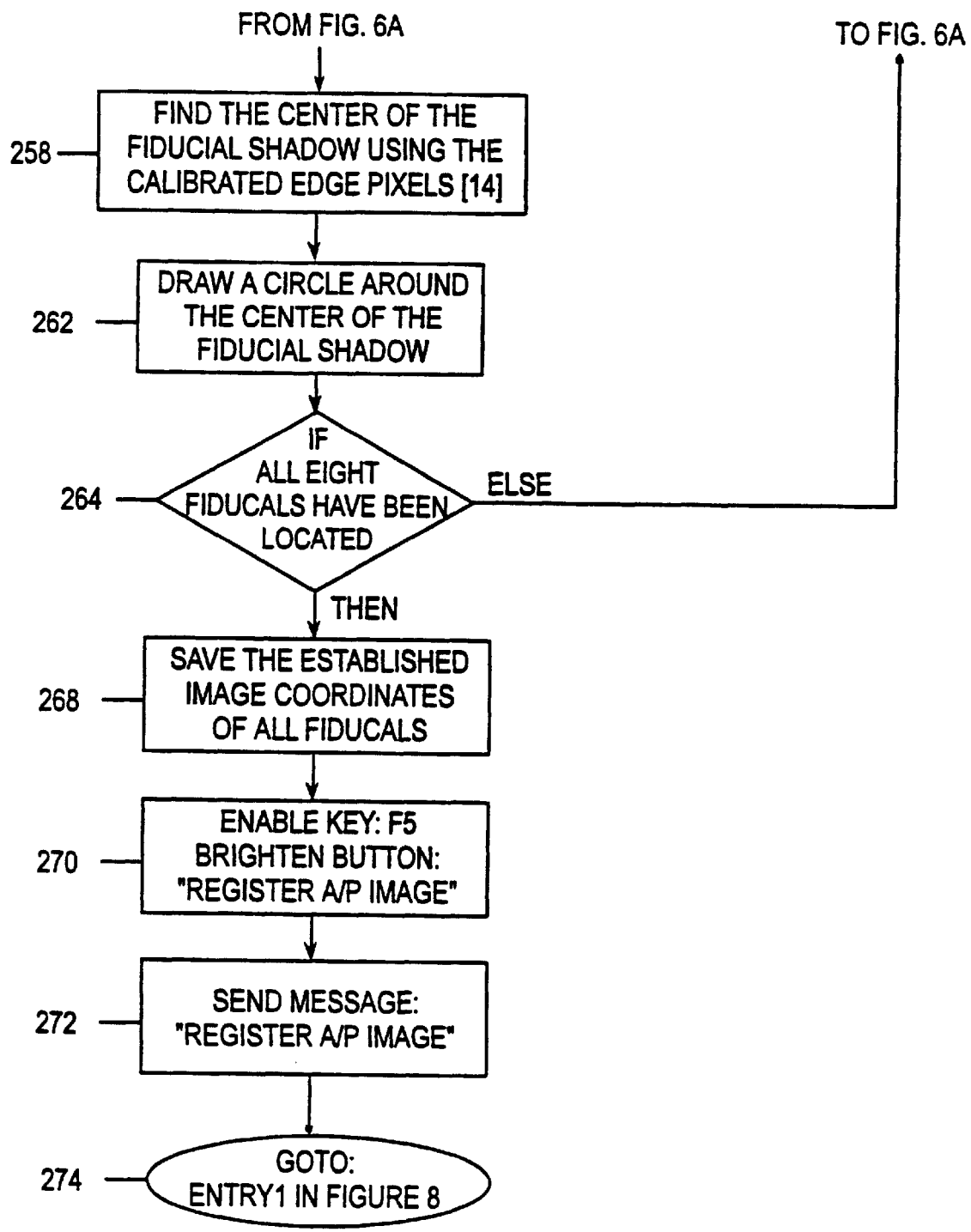

If the Select A/P Fiducials button 96 or the F3 key button is pressed, computer 40 advances to block 234 of FIG. 6A. Computer 40 first determines whether the A/P image is displayed on monitor 50 as illustrated at block 236. If not, computer 40 generates an error message, "Acquire A/P Image" as illustrated at block 238. Computer 40 then returns to wait for the next command as illustrated at block 240.

If the A/P image is displayed at block 236, computer 40 displays a square cursor on the display screen of monitor 50 as illustrated at block 242. Computer 40 then resets the number of located fiducials to zero as illustrated at block 244. Next, computer 40 waits for the trackball button to be clicked by the operator as illustrated as block 246. Once the trackball button is clicked over a fiducial shadow, computer 40 generates a beep as illustrated at block 248. Computer 40 then performs edge detection around the selected mouse cursor coordinate as illustrated at block 250. Such edge detection is performed using a gradient base method developed by John Canny and described in the article referenced in Section [1] of the attached Appendix. Such article is hereby incorporated by reference and made a part of this detailed description.

Computer 40 then determines whether at least 3 edge pixels were found during the edge detection step as illustrated at block 252. If not, computer 40 generates an error message of "Try Again Closer to the Fiducial" as illustrated at block 254. Computer 40 then returns to block 246 to wait for the mouse button to be clicked again. If at least three edge pixels were found at block 252, computer 40 maps the edge pixels to their calibrated image coordinates using equation [13] from the attached Appendix as illustrated at block 256.

Computer 40 then finds the center of the fiducial shadow generated by the fiducials 26 using the calibrated edge pixels as set forth in equation [14] of the Appendix. This step is illustrated at block 258. Computer 40 then advances to block 262 of FIG. 6B. From block 262, computer 40 draws a circle around the center of the fiducial shadow.

Computer 40 then determines whether all eight of the fiducials 26 have been located in the A/P image as illustrated at block 264. If not, computer 40 returns to block 246 of FIG. 6A and then waits for the mouse button to be clicked again over a different fiducial shadow.

If all eight fiducials have been located at block 264, computer 40 then saves the established image coordinates of all the fiducials in the computer memory as illustrated at block 268. Computer 40 then enables and brightens the Register A/P Image Button 98 and F5 key as illustrated at block 270. Computer 40 then transmits the message "Register A/P Image" as illustrated at block 272.

Next, computer 40 automatically advances to location ENTRY1 of FIG. 8 as illustrated at Block 274. Computer 40 does not wait for an operator to press a button to move to location ENTRY1 of FIG. 8.

Figure 7A:
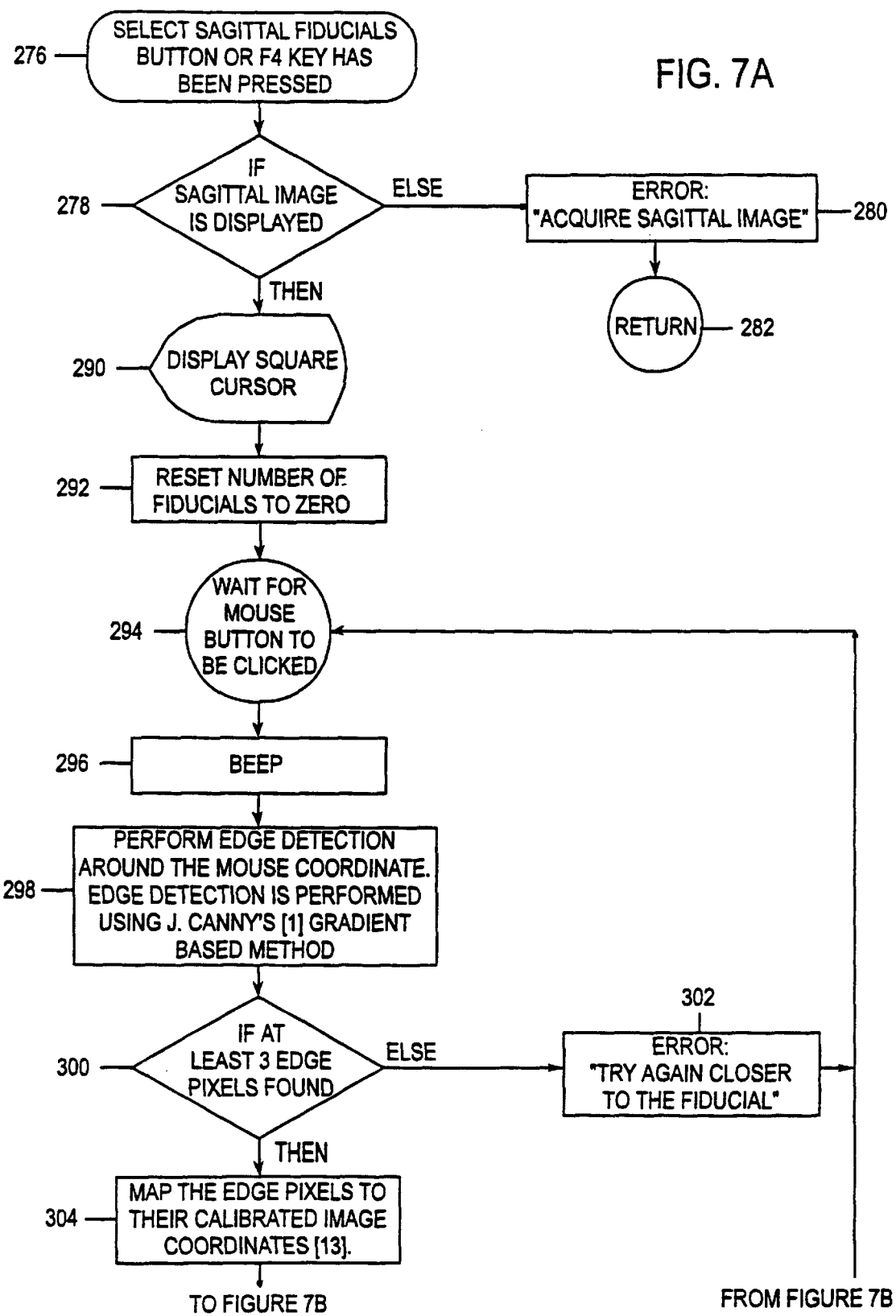
FIGS. 7A and 7B are flow charts of the steps performed by the computer and the user to select or identify sagittal fiducials displayed on the sagittal image of FIG. 3b.
Figure 7B:
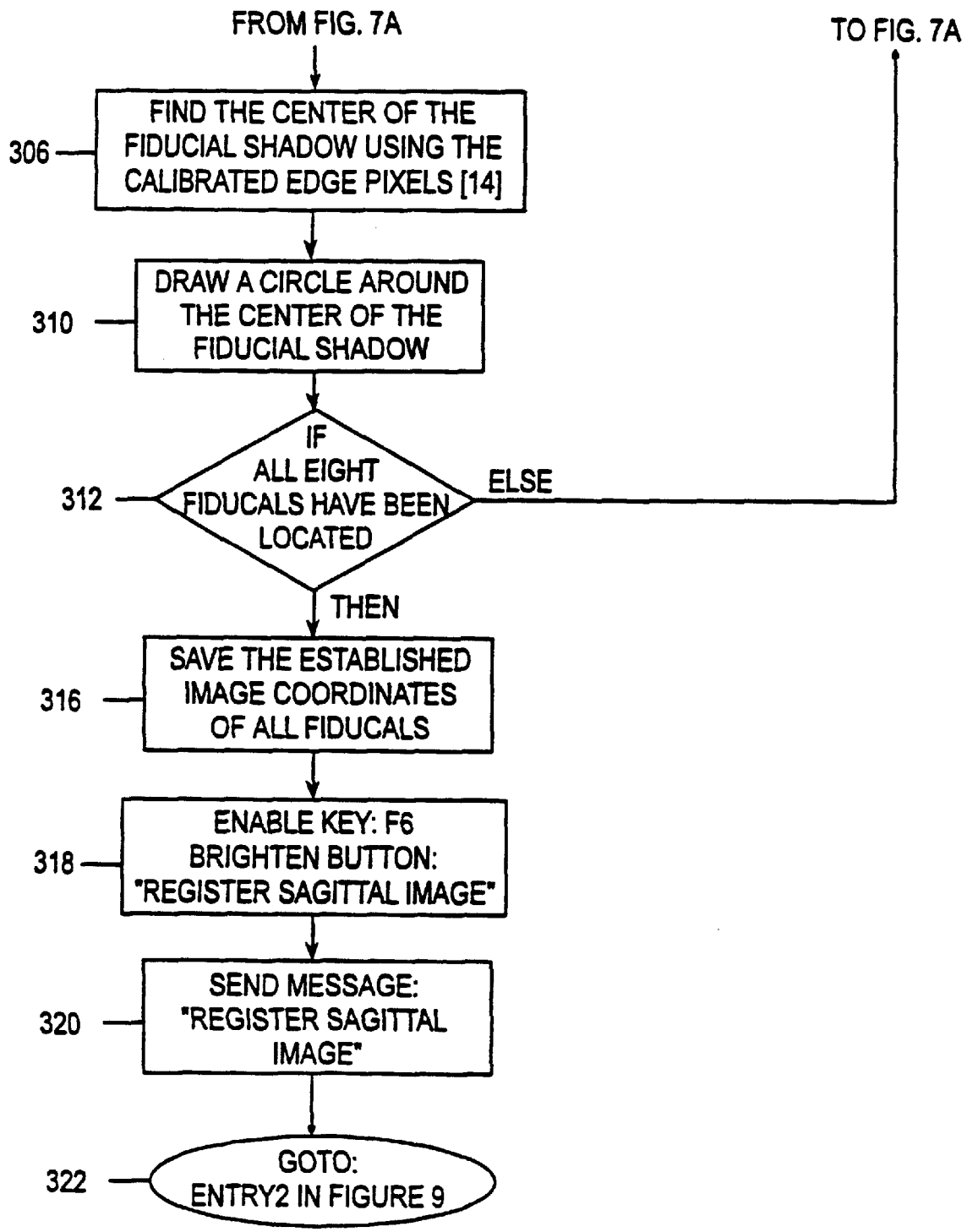

If the Select Sagittal Fiducials or the F4 key button is pressed, computer 40 advances to block 276 of FIG. 7A. Computer 40 first determines whether the sagittal image is displayed on monitor 48 as illustrated at block 278. If not, computer 40 generates an error message, "Acquire Sagittal Image" as illustrated at block 280. Computer 40 then returns to wait for the next command as illustrated at block 282.

If the sagittal image is displayed at block 278, computer 40 displays a square cursor on the display screen of monitor 48 as illustrated at block 290. Computer 40 then resets the number of located fiducials to zero as illustrated at block 292. Next, computer 40 waits for the trackball button to be clicked by the operator as illustrated as block 294. Once the trackball button is clicked, computer 40 generates a beep as illustrated at block 296. Computer 40 then performs edge detection around the selected trackball cursor coordinate as illustrated at block 298. Such edge detection is performed using a gradient base method developed by John Canny and described in the article referenced in Section [1] of the attached Appendix.

Computer 40 then determines whether at least 3 edge pixels were found during the edge detection step as illustrated at block 300. If not, computer 40 generates an error message of "Try Again Closer to the Fiducial" as illustrated at block 302. Computer 40 then returns to block 294 to wait for the trackball button to be clicked again. If at least three edge pixels were found at block 300, computer 40 maps the edge pixels to their calibrated image coordinates using equation [13] from the attached Appendix as illustrated at block 304.

Computer 40 then finds the center of the fiducial shadow generated by the fiducials 26 using the calibrated edge pixels as set forth in equation [14] of the Appendix. This step is illustrated at block 306. Computer 40 then advances to block 310. From block 310, computer 40 draws a circle around the center of the fiducial shadow. Computer 40 then determines whether all eight of the fiducials 26 have been located in the sagittal image as illustrated at block 312. If not, computer 40 returns to block 294 and then waits for the trackball button to be clicked again.

If all eight fiducials have been located at block 312, computer 40 then saves the established image coordinates of all the fiducials in the computer memory as illustrated at block 316. Computer 40 then enables and brightens the Register sagittal Image Button 76 and the F6 key as illustrated at block 318. Computer 40 then transmits a message of "Register Sagittal Image" as illustrated at block 320.

Next, computer 40 automatically advances to location ENTRY2 of FIG. 9 as illustrated at block 322. Computer 40 does not wait for an operator to press a button to move to location ENTRY2 of FIG. 9.

If the Register A/P Image button 98 or the F5 key was pressed, computer 40 advances to block 324 of FIG. 8. Computer 40 first determines whether all of the A/P fiducials have been found as illustrated at block 326. If not, computer 40 generates an error message of "Haven't Selected All the Fiducials" as illustrated at block 328. Computer 40 then returns to wait for the next command as illustrated at block 330.

If all the A/P fiducials have been found at block 326, computer 40 advances to block 332. As discussed above, computer 40 also automatically advances to block 332 from block 274 of FIG. 6A after all the fiducials have been selected.

In block 332, computer 40 first recalls all the two-dimensional coordinates of the A/P fiducial centers. Next, the computer 40 reads in data from a file of the three-dimensional coordinates of the center of the fiducials 26 as illustrated at block 334. The three-dimensional coordinates of the fiducials 26 are obtained using a Coordinate Measurement Machine (CMM). Therefore, this data provides information related to the actual location of the fiducials 26. Typically, these CMMed coordinates are obtained from the manufacturer of the registration artifact 24.

Next, computer 40 optimizes the parameters of a geometric model which projects three dimensional coordinates into corresponding image points. The optimized model is encapsulated in a registration matrix as set forth in section [3]. Optimization is performed by minimizing (in a least squares sense) the deviation between the model's projections of the three-dimensional coordinates read at block 334, and the two-dimensional coordinates read at block 332. The Levenberg-Marquardt method is used for optimization, as described in equation [2] of the attached Appendix and as illustrated at block 336. Computer 40 then constructs a registration matrix as set forth in section [3] of the attached Appendix. This step is illustrated at block 338.

Computer 40 next determines whether the sagittal image has been registered as illustrated at block 340. If not, computer 40 generates a message of "Perform Sagittal Registration" as illustrated at block 342. Computer 40 then returns to wait for the next command as illustrated at block 344.

If the sagittal image has been registered at block 340, computer 40 generates a display message of "Pick Entry Point" as illustrated at block 346. Computer 40 then returns to wait for the next command as illustrated at block 348.

If the Register sagittal Image button 76 or the F6 key have been pressed, computer 40 advances to block 350 of FIG. 9. Computer 40 first determines whether all of the sagittal fiducials have been found as illustrated at block 352. If not, computer 40 generates an error message of "Haven't Selected All the Fiducials" as illustrated at block 354. Computer 40 then returns to wait for the next command as illustrated at block 356.

If all the sagittal fiducials have been found at block 352, computer 40 advances to block 358. As discussed above, computer 40 also automatically advances to block 358 from block 322 of FIG. 7B after all the fiducials have been selected.

In block 358, computer 40 first recalls all the two-dimensional coordinates of the sagittal fiducial centers. Next, the computer 40 reads in data from a file of the three-dimensional coordinates of the center of the fiducials 26 as illustrated at block 360. The coordinates of the fiducials 26 are obtained using a Coordinate Measurement Machine (CMM). Therefore, this data provides information related to the actual location of the fiducials 26. Typically, these coordinates are obtained from the manufacturer of the registration artifact 24.

Next, computer 40 optimizes the fit between the three-dimensional coordinates read at block 360 and the two-dimensional coordinates read at block 358 using the Levenberg-Marquardt method described in equation [2] of the attached Appendix as illustrated at block 362. Computer 40 then constructs a registration matrix as set forth in section [4] of the attached Appendix. This step is illustrated at block 364.

Computer 40 next determines whether the A/P image has been registered as illustrated at block 366. If not, computer 40 generates a message of "Perform A/P Registration" as illustrated at block 368. Computer 40 then returns to wait for the next command as illustrated at block 370.

If the A/P image has been registered at block 366, computer 40 generates a message of "Pick Entry Point" as illustrated at block 372. Computer 40 then returns to wait for the next command as illustrated at block 374.

Figure 10:
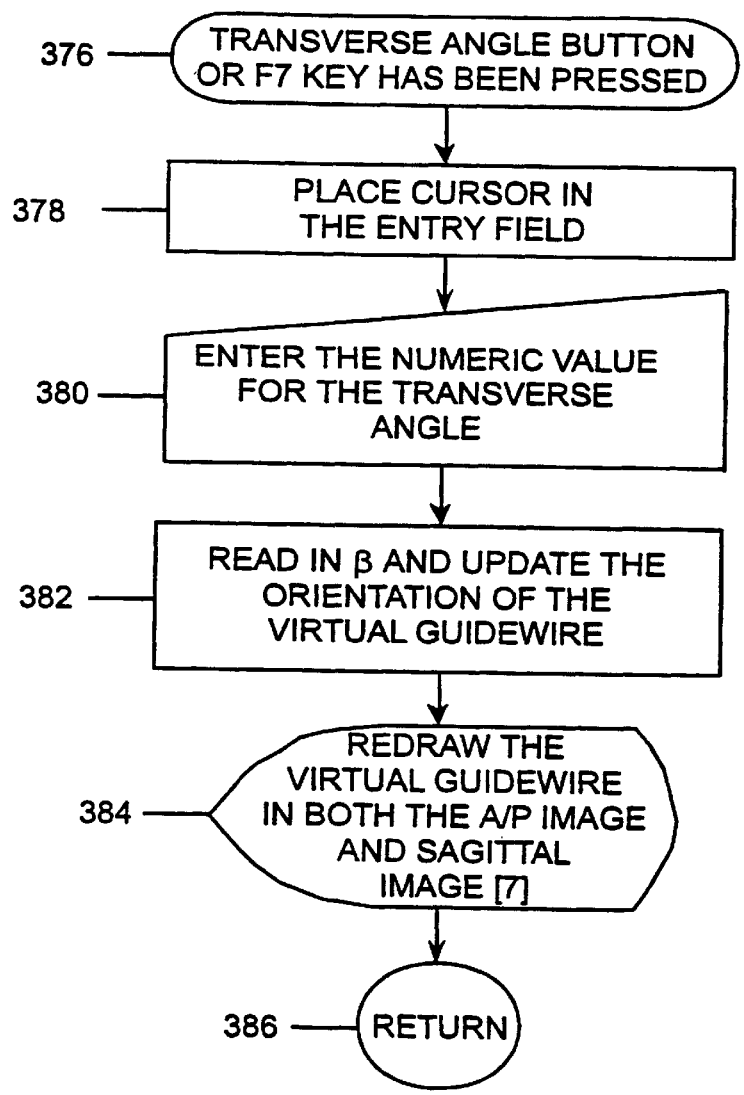
FIG. 10 is a flow chart illustrating the steps performed by the computer for changing a transverse angle of the virtual guidewire.

If the transverse angle button 100 or the F7 key is pressed, computer 40 advances to block 376 of FIG. 10. The transverse angle is the angle determined by using the right hand rule about the X axis 34 of FIG. 1. To adjust the transverse angle, the operator places the cursor in the Entry Field button 101 of FIG. 3a as illustrated at block 378 of FIG. 10. The operator then enters a numeric value for the transverse angle as illustrated at block 380. Computer 40 then reads the new transverse angle, and updates the orientation of the virtual guidewire using the equations set forth in section [6] of the attached Appendix. This step is illustrated at block 382. Next, computer 40 redraws the virtual guidewire projection 92 in the A/P image area 86 and 68 in the sagittal image area 62 based on the new transverse angle using the equation set forth in section [7] of the attached Appendix as illustrated at block 384. Computer 40 then returns to wait for the next command as illustrated at block 386.

Figure 11:
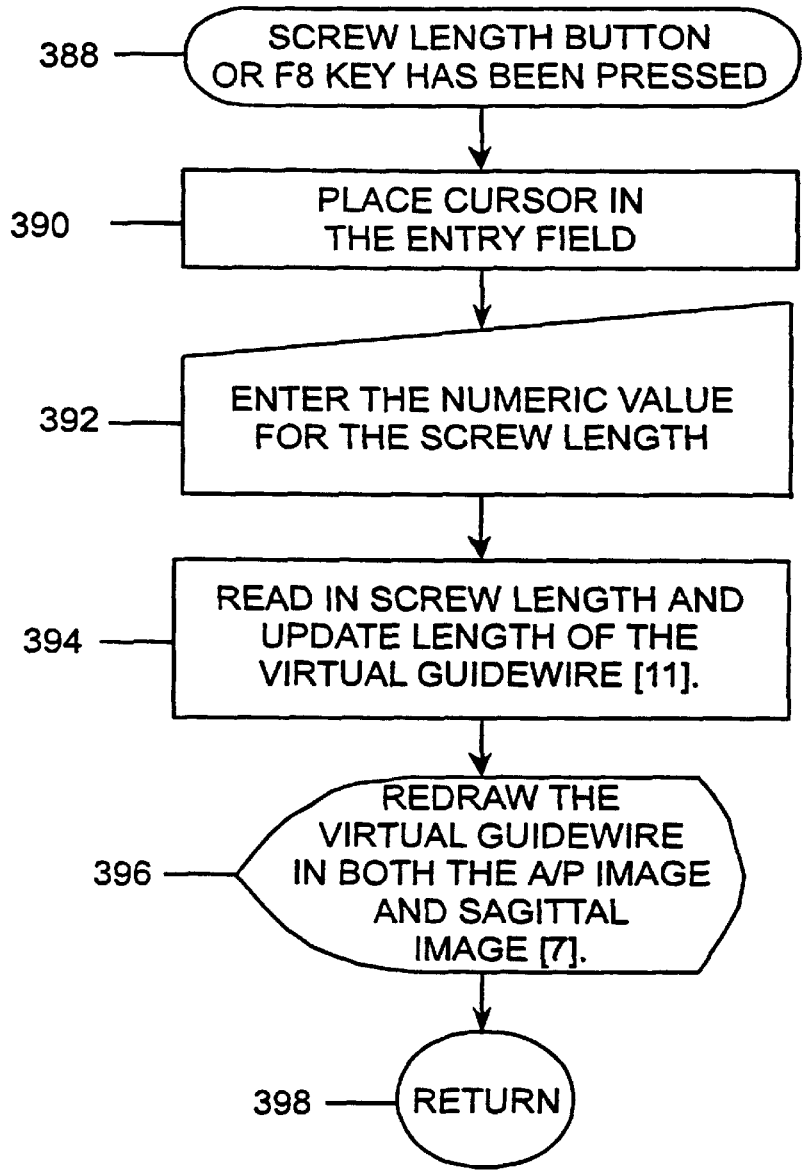
FIG. 11 is a flow chart illustrating the steps performed by the computer to change the length of the virtual guidewire used in the stereotactic surgical procedure.

If the Screw Length button 80 or the F8 key was pressed, computer 40 advances to block 388 of FIG. 11. The cursor is then placed on the entry field 81 of FIG. 3b as illustrated at block 390. The operator then enters the numeric value for the new screw length as illustrated at block 392. Computer 40 reads the new screw length, and updates the length of the virtual guidewire using the equations set forth in section [11] of the Appendix. This step is illustrated at block 394. Next, computer 40 redraws the projected guidewire 92 in the A/P image area 86 and the projected guidewire 68 in the sagittal image area 62 using the equations set forth in section [7]0 of the Appendix. These steps are illustrated at block 396. Next, computer 40 returns to wait for the next command as illustrated at block 398.

Figure 13:
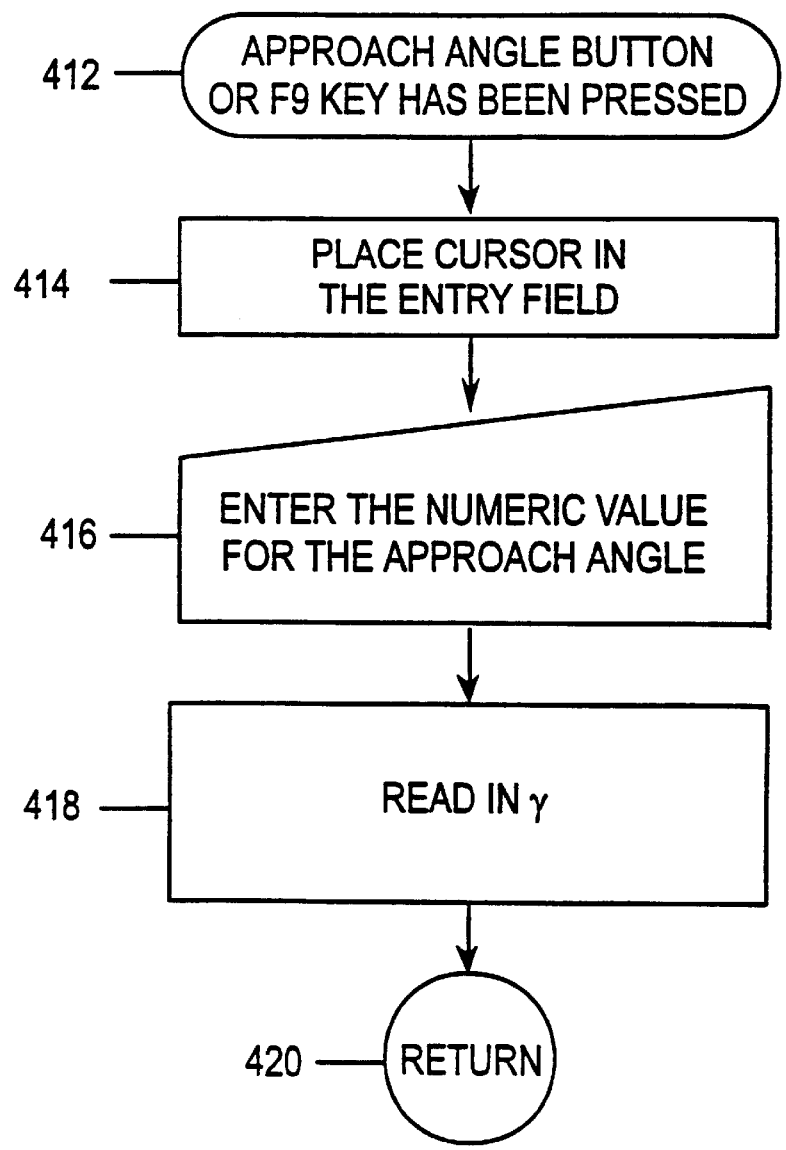
FIG. 13 is a flow chart illustrating the steps performed by the computer to change the approach angle of the robot.

If the Sagittal Angle button 78 or the F10 key is pressed, computer 40 advances to block 400 of FIG. 13 to adjust the sagittal angle. The sagittal angle is the angle about the Y-axis 36 of FIG. 1 using the right hand rule.

The cursor is placed in an entry field 79 of FIG. 3b as illustrated at block 402. Next, the operator enters a numeric value for the sagittal angle as illustrated at block 404. Computer 40 then reads the value of the new sagittal angle, and updates the orientation of the virtual guidewire using the equations set forth in section [10] of the Appendix. These steps are illustrated at block 406. Next, computer 40 redraws the projected guidewire 92 in the A/P image area 86 and the projected guidewire 68 in the sagittal image area 62 using the equations set forth in section [7] of the Appendix. These steps are illustrated at block 408. The computer 40 then returns to wait for the next instruction as illustrated at block 410.

Figure 12:
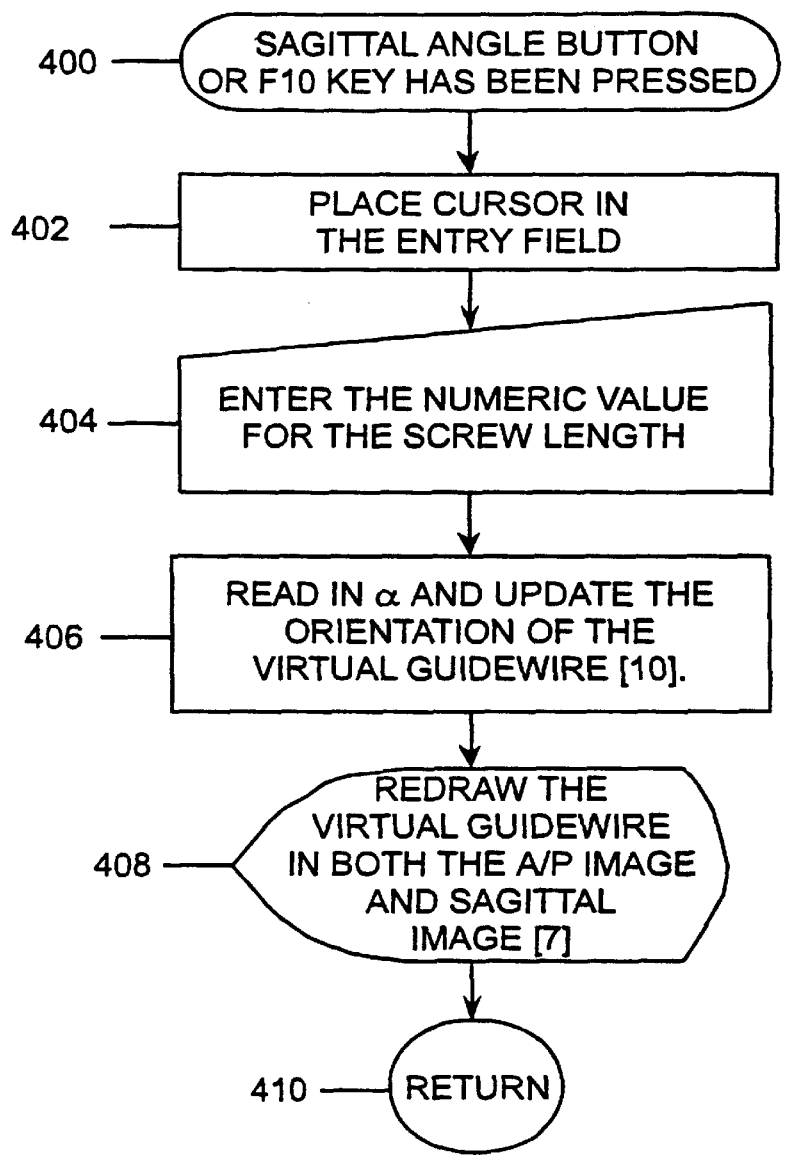
FIG. 12 is a flow chart illustrating the steps performed by the computer to change a sagittal angle of the virtual guidewire.

If the Approach Angle button 102 or the F9 key was pressed, computer 40 advances to block 412 of FIG. 12. The approach angle is the angle taken about the Z-axis 38 of FIG. 1 using the right hand rule.

The cursor is placed in the entry field 103 of FIG. 3a as illustrated at block 414. The operator then enters a numeric value for the new approach angle as illustrated at block 416. The computer 40 then reads the new approach angle as illustrated at block 418. Computer 40 then returns to wait for the next command as illustrated at block 420.

In order to plan a linear trajectory in space, only two angles are needed, for this particular procedure the transverse angle and the sagittal angle are used. The approach angle permits the surgeon to control movement of the robot. In other words, the approach angle is not used with the planning of the trajectory.

Figure 14:
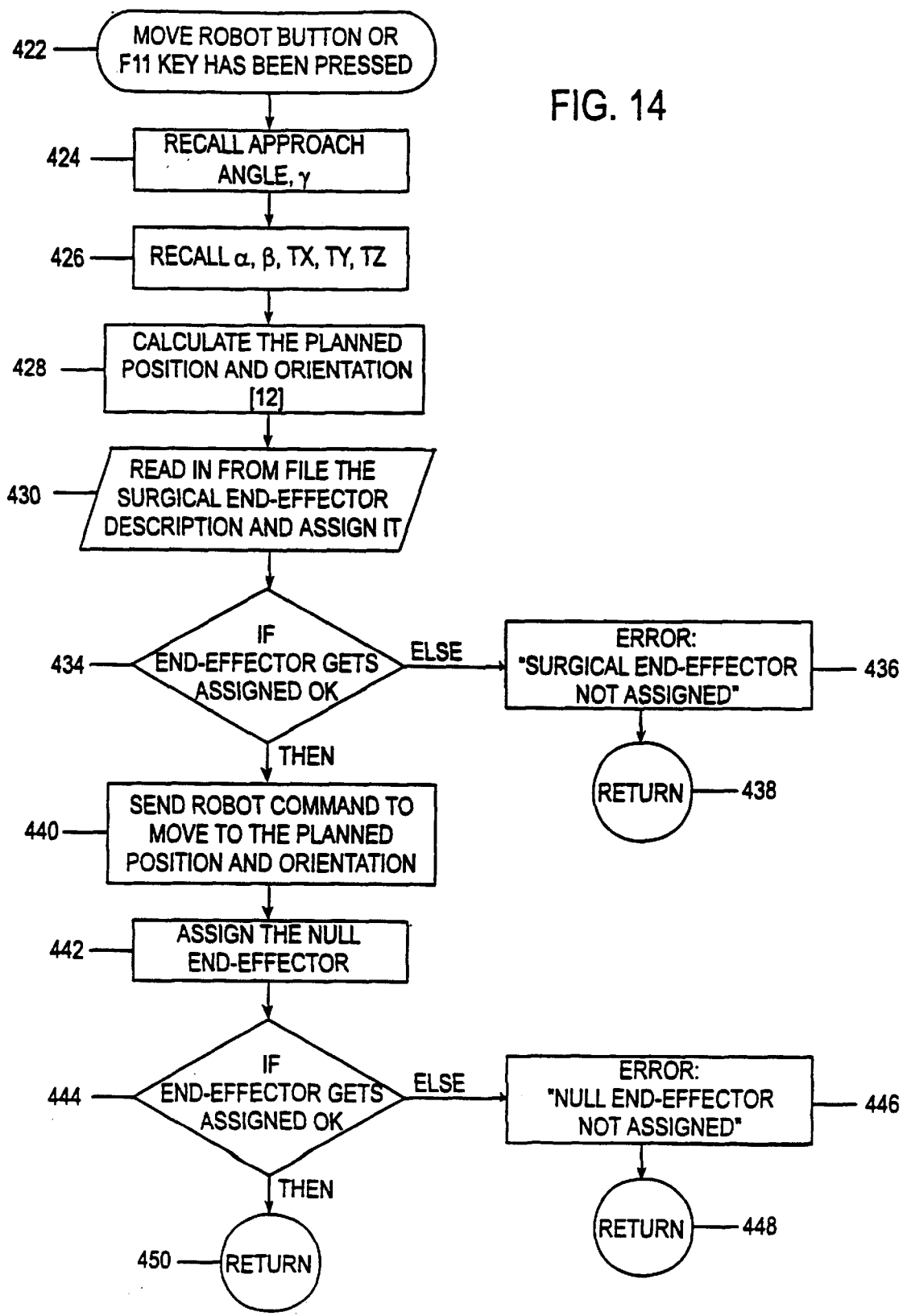
FIG. 14 is a flow chart illustrating the steps performed by the computer to move the robot illustrated in FIG. 1 to the planned position and orientation.

If the Move Robot button 104, or the F11 key are pressed, computer 40 advances to block 422 of FIG. 14. Computer 40 first recalls the approach angle from memory as illustrated at block 424. Next, computer 40 recalls the sagittal angle, the transverse angle and the three-dimensional coordinates of the top point of the virtual guidewire as illustrated at block 426. Next, computer 40 calculates the planned position and orientation using the equations in section [12] of the Appendix. This step is set forth at block 428. Next, computer 40 reads in data from a file related to the specific surgical end-effector being used for the surgical procedure as illustrated at block 430. This data includes the three-dimensional coordinates from the Coordinate Measurement Machine (CMM).

Computer 40 determines whether the surgical end-effector is properly assigned at block 434. If not, computer 40 generates an error message of "Surgical end-effector Not Assigned" as illustrated at block 436. Computer 40 then returns to wait for the next command as illustrated at block 438.

If the surgical end-effector is properly assigned at block 434, computer sends a command through serial communication port 50 to the robot controller 53 to move the robot to the planned position and orientation as illustrated at block 440. Computer 40 assigns the "NULL" end-effector as illustrated at block 442. Computer 40 determines whether the NULL end-effector was properly assigned at block 444. If not, computer 40 generates an error message of "NULL end-effector Not Assigned" as illustrated at block 446. Computer 40 then returns to wait for the next command at block 448. If the NULL end-effector is properly assigned at block 444, computer 40 returns to wait for the next command as illustrated at block 450.

Figure 15:
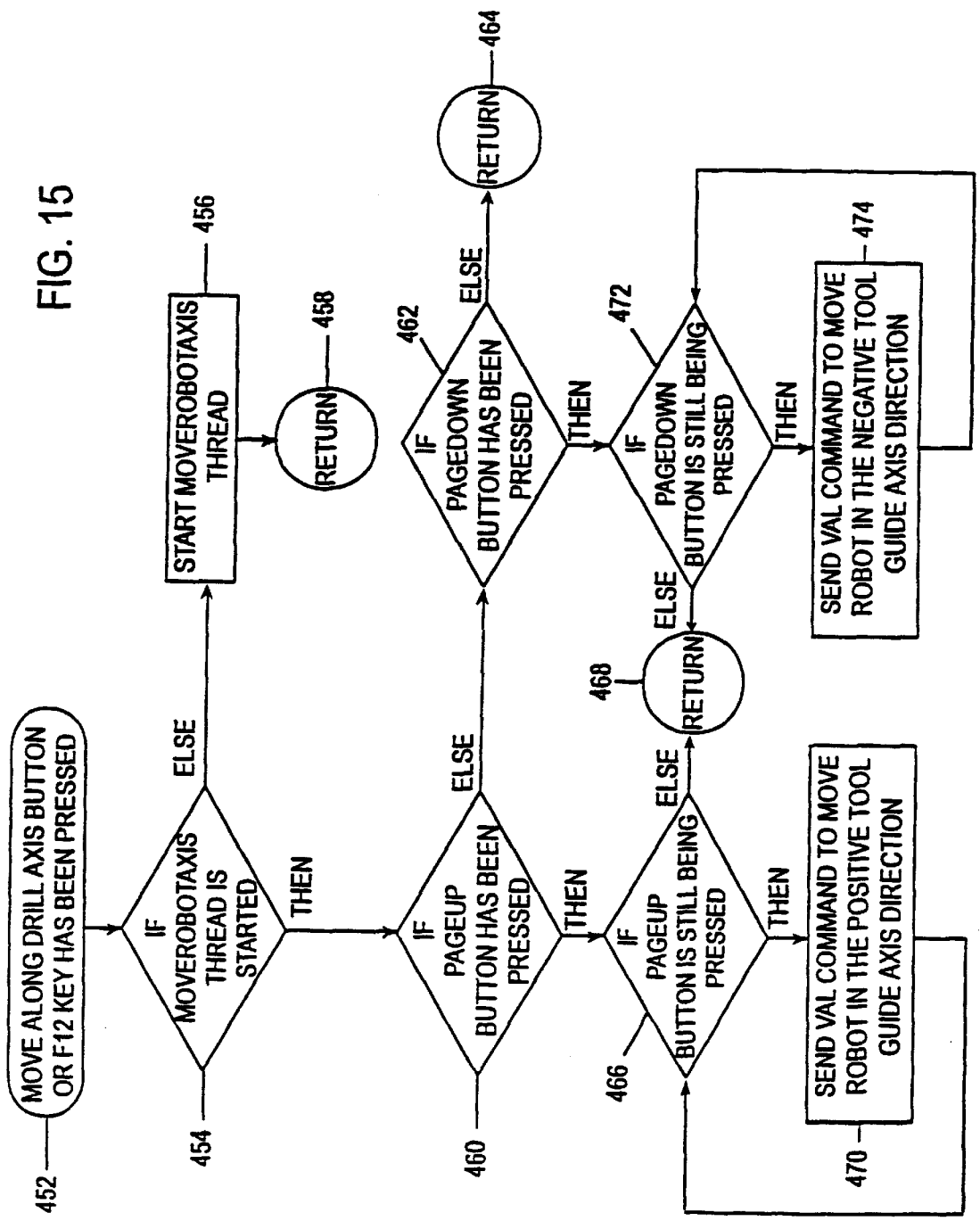
FIG. 15 is a flow chart illustrating the steps performed by the computer to move the end effector of the robot along the axis of the tool guide.

If the Move Robot Along Axis button 82 of FIG. 3b is selected, computer 40 advances to block 452 of FIG. 15. The computer 40 has already moved the robot to the proper orientation during the steps of FIG. 20. Therefore, the steps of FIG. 21 are designed to move the robot along the tool guide axis defined by the tool guide 28 of FIG. 2. The tool guide axis typically moves toward and away from the body on the table 14 along the tool guide axis. Computer 40 determines whether a thread entitled "Move Robot Axis" has been dispatched at block 454. This thread program runs by itself until it is stopped. If the program is not started at block 454, computer 40 starts this program as illustrated at block 456. Computer 40 then returns to wait for additional instructions at block 458. If the thread program has started at block 454, then computer determines whether the Page Up button has been pressed at block 460. If not, computer 40 determines whether the Page Down button has been pressed at block 462. If not, computer 40 returns to block 464 to wait for the next command.

If the Page Up button was pressed at block 460, computer 40 determines whether the Page Up button is still being pressed at block 466. If not, computer 40 returns to wait for the next command as illustrated at block 468. If the Page Up button is still being pressed at block 466, computer 40 sends a VAL command from communication port 50 to robot controller 53 to move the robot in the positive tool guide axis direction as illustrated at block 470. The positive tool guide axis direction is up away from the patient. Computer 40 then returns to block 466.

If the Page Down button has been pressed at block 462, computer 40 determines whether the Page Down button is still being pressed at block 472. If not, computer 40 returns at block 468 to wait for the next command. If the Page Down button is still being pressed at block 472, computer 40 sends a VAL command to move the robot in the negative tool guide axis direction as illustrated at block 474. The negative tool guide axis direction is down toward the patient. Computer 40 then returns to block 472.

In other words, the control steps of FIG. 15 permit the operator to move the robot along its tool guide axis. Once the robot is moving in either the positive or negative direction, it keeps moving until the Page Up or Page Down are released. The entire robot moves in order to maintain the end-effector 24 and the tool guide 28 in the same orientation along the planned axis. In other words, the end-effector 24 of robot 18 may be maintained in an orientation that is 45° relative to Z-axis 38 of FIG. 1. VAL is the program control language for the PUMA-560 controller 53. It is understood that other robots, controllers, and program languages may be used in accordance with the present invention.

Figure 16A:
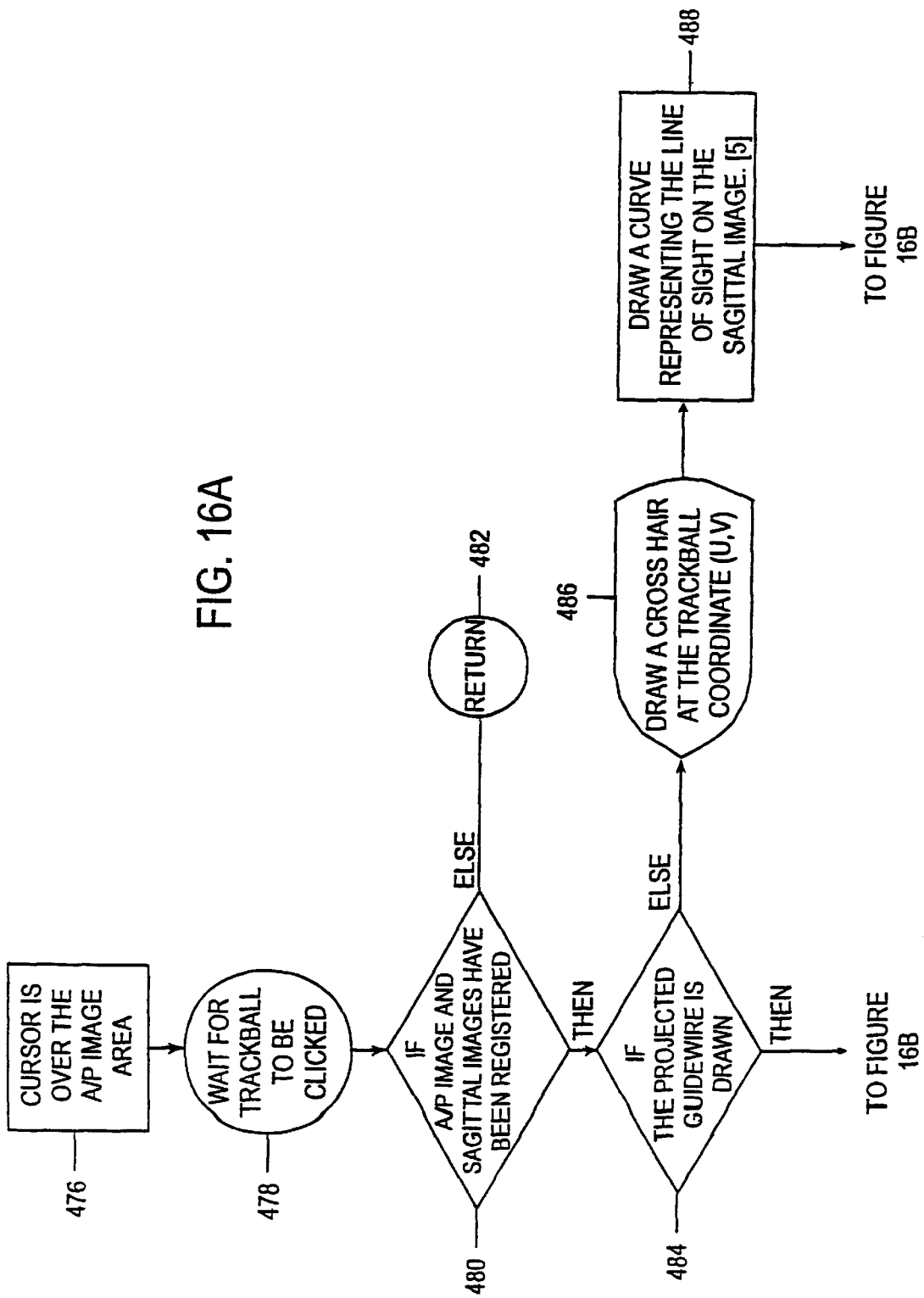
Figure 16B:
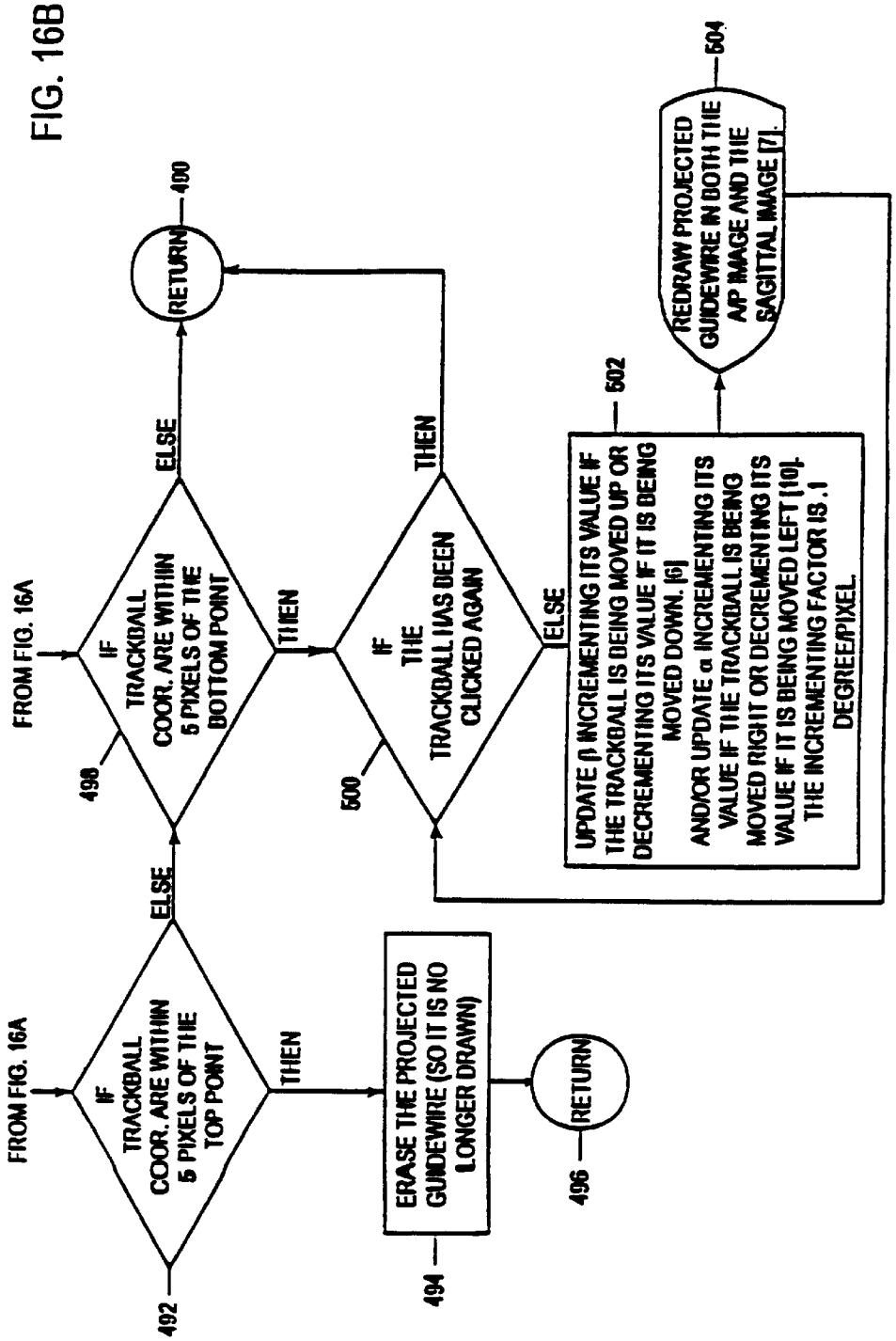

If a cursor is over the A/P image area 86 of FIG. 3a, computer 40 advances to block 476 of FIG. 16A. Computer 40 waits for the trackball to be clicked in the A/P image area 86 as illustrated at block 478. Once the trackball has been clicked at block 478, computer 40 determines whether both the A/P image and the sagittal image have been registered as illustrated at block 480. If not, computer 40 does nothing and returns to block 482 to wait for the next command.

If the A/P and the sagittal images have been registered at block 480, computer 40 determines whether the projected guidewire is drawn as illustrated at block 484. If not, computer 40 assumes that the operator intends to draw the projected guidewire. Therefore, the computer 40 draws a cross hair at trackball coordinate (U,V) as illustrated at block 486. Next, computer 40 draws a curve representing the line of site on the sagittal image using the equations of section [5] of the attached Appendix as illustrated at block 488. A curve is drawn representing the line of site due to the distortion in the images. If you take an x-ray of a straight line, its image will be a curve due to the distortions inherent in the fluoroscope's image intensifier. This is why a curve must be drawn to represent the line of sight. Once the line of sight indicator 70 is drawn on the sagittal image area 62 of FIG. 3b, computer 40 returns to wait for the next command as illustrated at block 490.

If the projected guidewire is already drawn at block 484, computer 40 determines whether the trackball coordinates are within five pixels from the top point 88 in the A/P image area 86. This step is illustrated at block 492. If the cursor coordinates are within five pixels from the top point 88, computer 40 erases the projected guidewire as illustrated at block 494 and returns to wait for the next command as illustrated at block 496.

If the trackball cursor coordinates are not within five pixels from the top point 88 at block 492, computer 40 determines whether the trackball coordinates are within five pixels of the bottom point 90 as illustrated at block 498. If not, computer 40 returns to wait for the next command as illustrated at block 490. If the trackball cursor coordinates are within five pixels from the bottom point 90 at block 498, computer 40 determines whether the trackball has been clicked again as illustrated at block 500. If so, computer 40 returns to block 490 to wait for the next command. If not, computer 40 updates the transverse or sagittal angle as illustrated at block 502 based on movement of the trackball. The transverse angle value is incremented if the trackball is being moved up. The transverse angle value is decreased if the trackball is moving down. The sagittal angle value is incremented if the trackball is being moved right. The sagittal angle value is decreased if the trackball is moving left. The incrementing factor is 0.1° per pixel. The equations for this step are set forth in section [6] of the Appendix.

After the transverse and/or sagittal angle have been updated at block 502, computer 40 redraws the projected guidewire 92 in the A/P image area 86 and the projected guidewire 68 in the sagittal image area 62 using the equations in section [7] of the attached Appendix. These steps are illustrated at block 504. Computer 40 then returns to block 500.

Figure 17A:
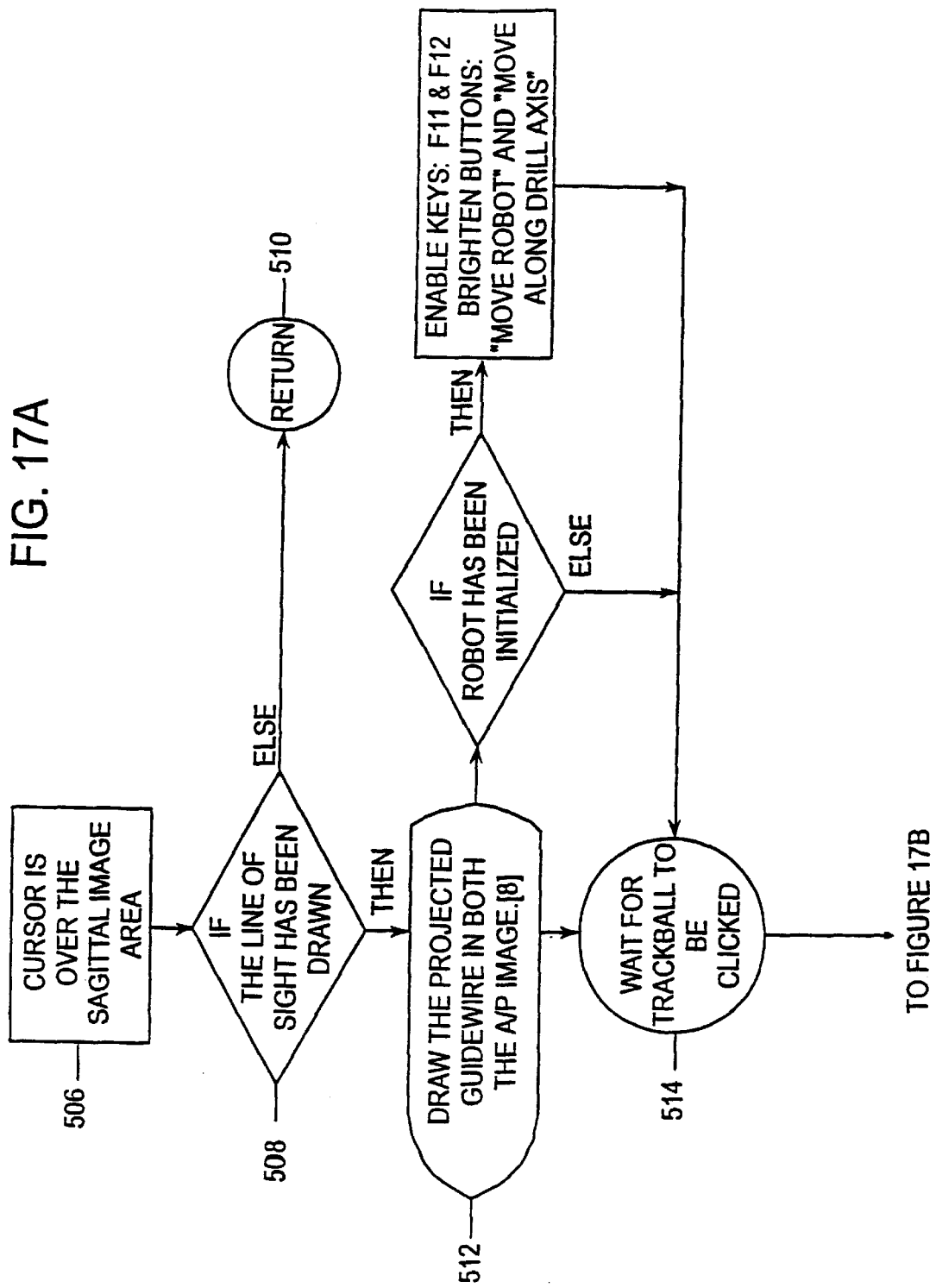

If the cursor is over the sagittal image area 62 of FIG. 3b, computer 40 advances to block 506 of FIG. 17A. Computer 40 determines whether the line of sight has been drawn at block 508. If not, computer 40 returns to wait for the next command at block 510. If the line of sight has been drawn at block 508, computer 40 draws the projected guidewire 92 in the A/P image area 86 and the projected guidewire 68 in the sagittal image area 62 using the equations in section [8] of the Appendix. These steps are illustrated at block 512. Computer 40 also checks if the robot has been initialized at block 513, if it has then computer 40 enables and brightens buttons "Move Robot" 104, and "Move Along Drill Axis" 82, and keys F11, and F12 at block 513.5. Next, computer 40 waits for the track ball in the sagittal image area 62 to be clicked as illustrated at block 514. If robot has not been initialized then computer 40 waits for the track ball in the sagittal image area 62 to be clicked as illustrated at block 514. Next, computer 40 determines whether the trackball cursor coordinates are within five pixels from the top point 64 as illustrated at block 516. If not, computer 40 determines whether the trackball coordinates are within five pixels of the bottom point 66 as illustrated at block 518. If not, computer 40 returns at block 520 to wait for the next command.

If the trackball coordinates are within five pixels of the top point 64 at block 516, computer 40 determines whether the trackball has been clicked again at block 522. If so, computer 40 returns at block 524 to wait for the next command. If not, computer 40 updates the position of the virtual guidewire 68 by moving it along the line of sight in the same direction as the trackball movements. The incrementing ratio is 0.1° mm/pixel. This step is illustrated at block 526. The computer uses the equations set forth in section [9] of the Appendix to update the virtual guidewire position. Computer 40 then redraws the projected guidewire 68 in the sagittal image area 62 and also redraws the projected guidewire 92 in the A/P image area 86 as illustrated at block 528 by using the equations set forth in Section [7] of the Appendix. Computer 40 then returns back to block 522.

If the trackball coordinates are within five pixels from the bottom point 66 at block 518, computer 40 determines whether the trackball has been clicked again at block 530. If so, computer 40 returns at block 524 to wait for the next command. If not, computer 40 assumes that the operator wants to adjust the position of bottom point 66. Therefore, computer 40 updates the sagittal and/or transverse angle as illustrated at block 532 based on movement of the trackball. The transverse angle value is incremented if the trackball is being moved up. The transverse angle value is decreased if the trackball is moving down. The sagittal angle value is incremented if the trackball is being moved to the right. The sagittal angle value is decreased if the trackball is moving to the left. The incrementing ratio is 0.1° /pixel. Computer 40 uses the equations of section [10] of the Appendix for these steps as illustrated at block 532. Next computer 40 redraws the projected guidewire 68 in the sagittal image area 62 and the projected guidewire 92 in the A/P image area 86 as illustrated at block 534 using the equations set forth in Section [7] of the Appendix. Computer 40 then returns to block 530.

Figure 18A:
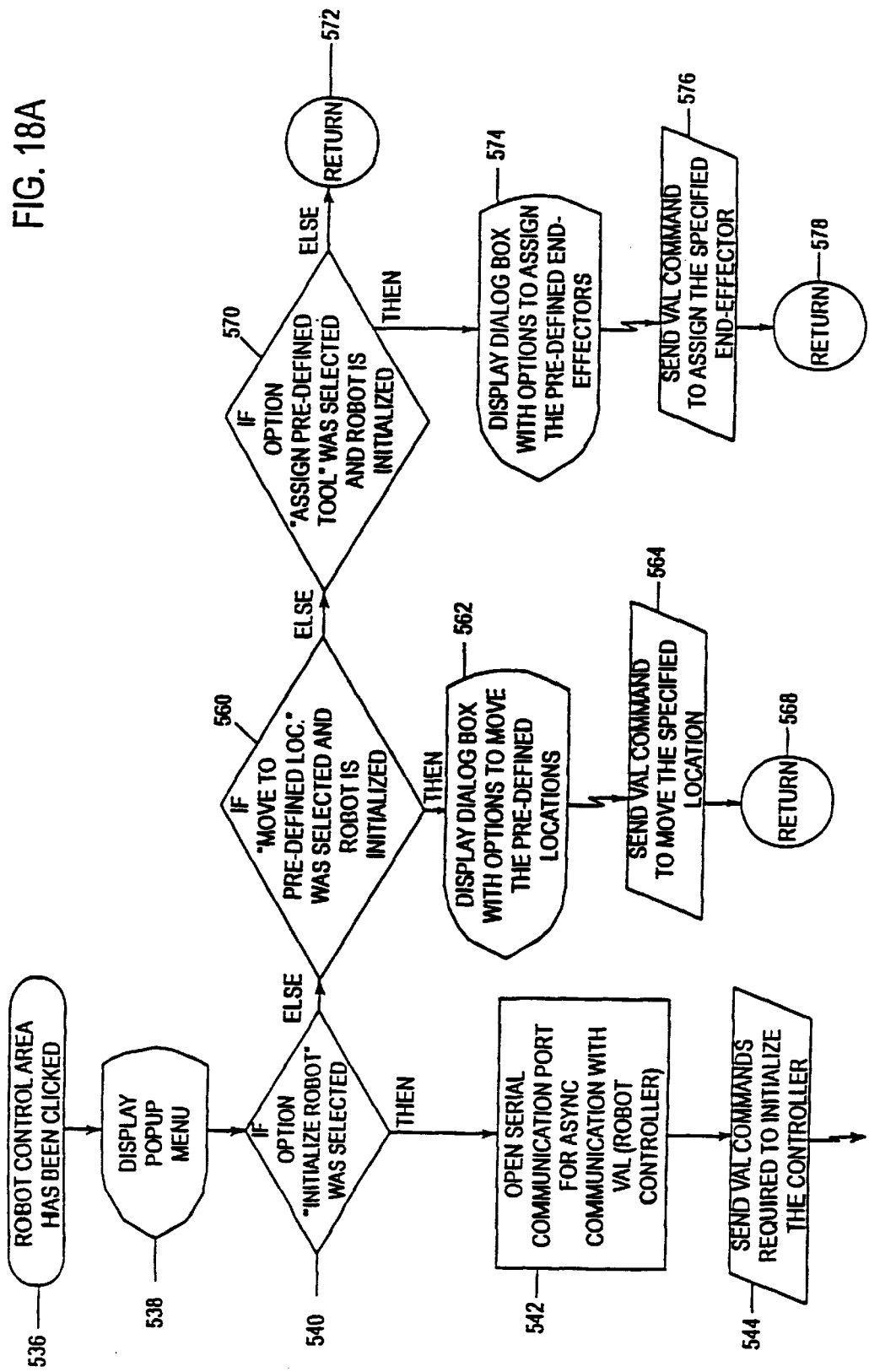
FIGS. 18A and 18B are flow charts illustrating the steps performed by the computer when the computer receives a user input based on a cursor in the robot control areas of FIGS. 3a–b.
Figure 18B:
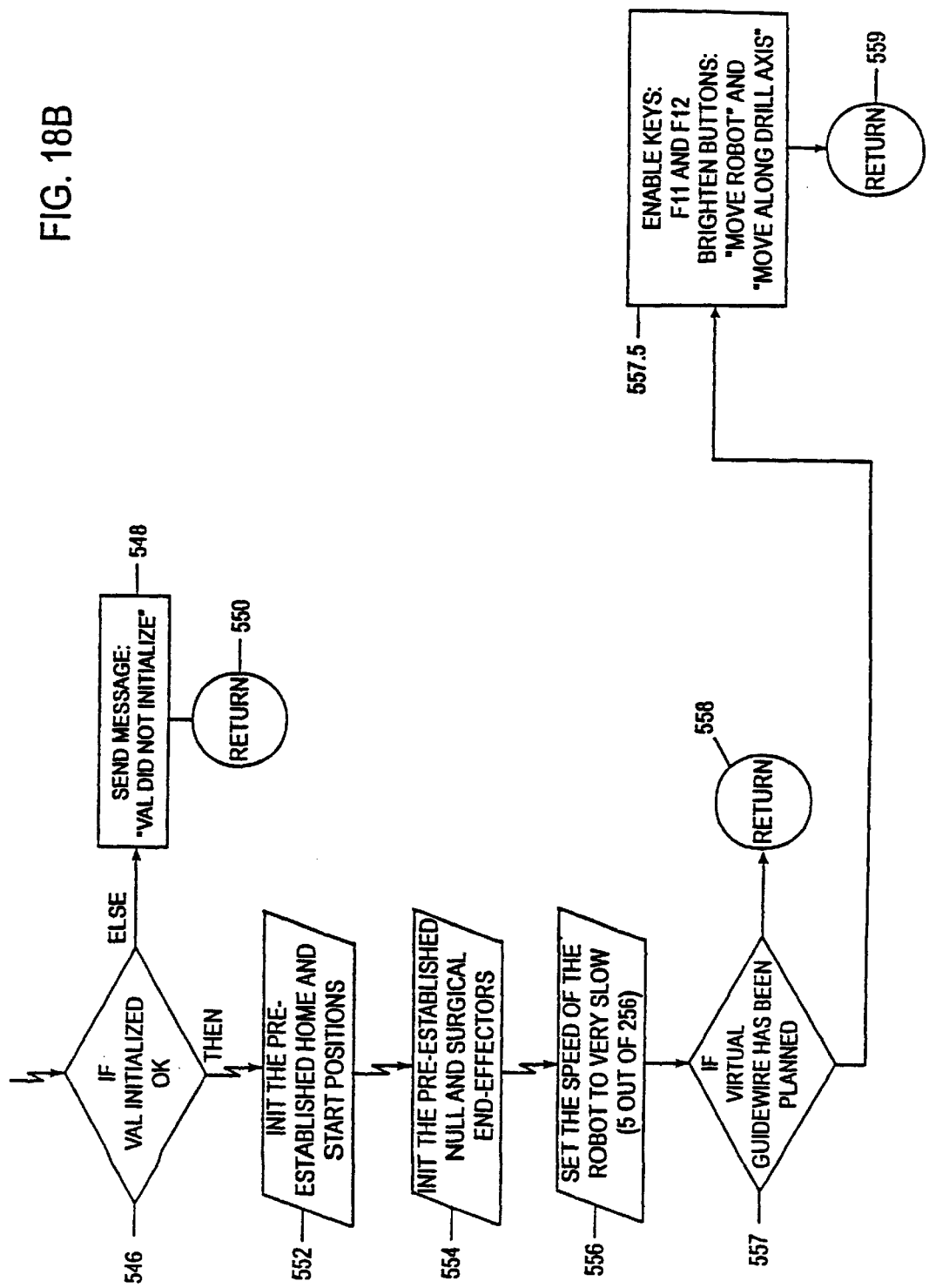

If the Robot Control areas 84 of FIG. 3a–b is selected, computer 40 advances to block 536 of FIG. 18A. Computer 40 then displays a menu giving the user options at block 538. The first option is a "Initialize Robot" option. Computer 40 determines whether the Initialize Robot menu item was selected at block 540. If so, computer 40 opens the serial communication port 52 for communication with the robot controller 53 as illustrated at block 542. Computer 40 sends the VAL program language commands required to initialize the robot controller 53 as illustrated at block 544. Computer 40 determines whether VAL was initialized properly at block 546. If VAL was not initialized properly then the computer 40 sends message VAL not initialized 53 as illustrated at block 548. Computer 40 then returns at block 550.

If VAL was properly initialized at block 546, computer 40 transmits preestablished HOME and START positions to the robot controller 53 as illustrated at block 552. The HOME and START position are two positions in the work space of the robot. In addition, computer 40 initializes the preestablished NULL end-effector and SURGICAL end-effector as illustrated at block 554. In other words, computer 40 sends specifications to the precise configurations of the specific surgical instrument that is going to be used. Therefore, the controller 53 is programmed to move the robot to these positions. During operation, computer 40 can instruct the controller 53 to move to the particular HOME or START positions. In addition, controller 53 will recognize instructions for the particular surgical end-effector which was initialized during step 554. Next, the robot speed is set to a very slow speed as illustrated at block 556. For example, the robot speed is set to a speed of 5 out of 256. Next, the computer 40 checks if the virtual guidewire has been planned, if it has then it enables and brightens buttons "Move Robot" 104 and "Move Robot Along Tool Axis" 82 and keys F11, F12, as illustrated in block 557.5. Computer 40 then returns to wait for the next instruction as illustrated at block 559.

If the virtual guidewire has not been planned, computer 40 then returns to wait for the next instruction as illustrated at block 558.

If an option entitled "Move to a Predefined Location" was selected from the pop-up menu 538 and if the robot was already initialized as illustrated at block 560, then computer 40 displays a dialog box with options to move the robot to the predefined locations as illustrated at block 562. In other words, a dialog box with the options to move the robot to the HOME position or the START position are displayed. The operator can select one of these options at block 562. Computer 40 then sends a VAL command to controller 53 to move the robot 18 to the specified location as illustrated at block 564. Computer 40 then returns at block 568 to wait for the next command.

If computer 40 determines that the option "Assigned Predefined Tool" was selected from the menu 538 and if the robot has already been initialized as illustrated at block 570, then computer 40 displays a dialog box with options to assign the predefined tools established during the initialization step at block 554. This step is illustrated at block 574. In other words, computer 40 displays a dialog box for assigning either the NULL end-effector or the SURGICAL end-effector at block 574. Once the desired tool is selected, computer 40 transmits to VAL the command to assign the specified end-effector to controller 53 as illustrated at block 576. Computer 40 then returns to wait for the next command at block 578. If the assigned predefined end-effector item was not selected or the robot was not initialized at block 570, computer 40 returns at block 572 to wait for the next command.

Although the invention has been described in detail with reference to a certain preferred embodiment, variations and modifications exist within the scope and spirit of the present invention as described and defined in the following claims.

APPENDIX
(Page 1 of 6)

Notation used throughout the flowcharts:

| | |
|---|---|
| WCS | World Coordinate System |
| CCS | C-arm Coordinate System |
| $(x, y, z)$ | Used for 3D coordinates in WCS and the CCS. |
| $(x, y)$ | Used for calibrated image coordinates. |
| $(u, v)$ | Used for real image coordinates. |
| $\alpha$ | Sagittal Angle. |
| $\beta$ | Transverse Angle. |
| $\gamma$ | Approach Angle. |

Subscripts:

| | |
|---|---|
| w = WCS | Specifies the coordinate system. Only used with 3D |
| c = CCS | coodinate systems. |
| t = top | Specifies a point on the virtual guidewire. |
| b = bottom | |
| a = A/P | Specifies to what image the information pertains to. |
| s = Sagittal | |

[1] J. Canny; "A Computational Approach to Edge Detection"; IEEE Transactions on Pattern Analysis Machine Intelligence; Vol 8, Nov. 1986, pp. 679-698.

[2] Mathematics involved in performing the Levenberg-Marquardt optimization method:

$$R = \begin{bmatrix} \cos\phi\cos\theta & \cos\phi\sin\theta\sin\psi - \sin\phi\cos\psi & \cos\phi\sin\theta\cos\psi + \sin\phi\sin\psi \\ \sin\phi\cos\theta & \sin\phi\sin\theta\sin\psi + \cos\phi\cos\psi & \sin\phi\sin\theta\cos\psi - \cos\phi\sin\psi \\ -\sin\theta & \cos\theta\sin\psi & \cos\theta\cos\psi \end{bmatrix}$$

$$u_c(x_i; a) = \left(\frac{R_{11}x + R_{12}y + R_{13}z + t_x}{R_{31}x + R_{32}y + R_{33}z + t_z}\right) f$$

and $$v_c(x_i; a) = \left(\frac{R_{21}x + R_{22}y + R_{23}z + t_y}{R_{31}x + R_{32}y + R_{33}z + t_z}\right) f$$

$$\chi^2(x; a) = \sum_{i=0}^{8} ((u_i - u_c(x_i; a))^2 + (v_i - v_c(x_i; a))^2)$$

where $x_i = [x, y, z]_i$ are the 3D coordinates of the fiducials, $(u, v)$ are the 2D coordinates of the center of the fiducials. and $a = [\phi, \theta, \psi, t_x, t_y, t_z]$ are the six parameters that define a six degree-of-freedom pose.

[3] Once the fit has been performed I construct the homogeneous transformation matrix that corresponds to the optimized parameters $(a = [\phi, \theta, \psi, t_x, t_y, t_z])$ as follows:

$$REG_A = \begin{bmatrix} \cos\phi\cos\theta & \cos\phi\sin\theta\sin\psi - \sin\phi\cos\psi & \cos\phi\sin\theta\cos\psi + \sin\phi\sin\psi & px \\ \sin\phi\cos\theta & \sin\phi\sin\theta\sin\psi + \cos\phi\cos\psi & \sin\phi\sin\theta\cos\psi - \cos\phi\sin\psi & py \\ -\sin\theta & \cos\theta\sin\psi & \cos\theta\cos\psi & pz \\ 0 & 0 & 0 & 1 \end{bmatrix}$$

APPENDIX
(Page 2 of 6)

[4] Once the fit has been performed I construct the homogeneous transformation matrix that corresponds to the optimized parameters ($a = [\phi, \theta, \psi, t_x, t_y, t_z]$) as follows:

$$REG_B = \begin{bmatrix} \cos\phi\cos\theta & \cos\phi\sin\theta\sin\psi - \sin\phi\cos\psi & \cos\phi\sin\theta\cos\psi + \sin\phi\sin\psi & px \\ \sin\phi\cos\theta & \sin\phi\sin\theta\sin\psi + \cos\phi\cos\psi & \sin\phi\sin\theta\cos\psi - \cos\phi\sin\psi & py \\ -\sin\theta & \cos\theta\sin\psi & \cos\theta\cos\psi & pz \\ 0 & 0 & 0 & 1 \end{bmatrix}$$

[5] The line of sight is calculated in the following way:
The line of sight is bound by (0, 0, 0) and ($u_c, v_c, f$) in the CCS.
Note: ($u_c, v_c$) is the calibrated equivalent of ($u, v$). See [13]

$$\begin{bmatrix} LSx_{w1} & LSx_{w2} \\ LSy_{w1} & LSy_{w2} \\ LSz_{w1} & LSz_{w2} \\ 1 & 1 \end{bmatrix} = [REG_A]^{-1} \begin{bmatrix} u_c & 0 \\ v_c & 0 \\ f & 0 \\ 1 & 1 \end{bmatrix}$$

$$\begin{bmatrix} x_{cs1} & x_{cs2} \\ y_{cs1} & y_{cs2} \\ z_{cs1} & z_{cs2} \\ 1 & 1 \end{bmatrix} = [REG_A] \begin{bmatrix} LSx_{w1} & LSx_{w2} \\ LSy_{w1} & LSy_{w2} \\ LSz_{w1} & LSz_{w2} \\ 1 & 1 \end{bmatrix}$$

$$u_1 = \frac{x_{cs1}}{z_{cs1}} f \quad v_1 = \frac{y_{cs1}}{z_{cs1}} f$$

$$u_2 = \frac{x_{cs2}}{z_{cs2}} f \quad v_2 = \frac{y_{cs2}}{z_{cs2}} f$$

Due to the inherent distortion in the fluoroscopic images the line of sight is drawn as a curve image. This is done by *un-calibrating* 50 points on the line bound by ($u_1, v_1$) and ($u_2, v_2$) as in [15] and drawing a polyline through them.

[6] Recall that the virtual guidewire is a 3D object bound by ($0_{wt}, 0_{wt}, 0_{wt}$) and ($0_{wb}, 0_{wb}, -screwlength_{wb}$).
$\beta = \beta + 0.1 *$ (# pixels moved by the trackball)

$$\begin{bmatrix} Vx_{wt} & Vx_{wh} \\ Vy_{wt} & Vy_{wh} \\ Vz_{wt} & Vz_{wh} \\ 1 & 1 \end{bmatrix} = [T^1(\alpha, \beta, tx, ty, tz)] \begin{bmatrix} 0_{wt} & 0_{wb} \\ 0_{wt} & 0_{wb} \\ 0_{wt} & -screwlength_{wb} \\ 1 & 1 \end{bmatrix}$$

[7] With ($Vx_{wt}, Vy_{wt}, Vz_{wt}$) and ($Vx_{wh}, Vy_{wh}, Vz_{wh}$) the virtual guidewire's projection is drawn on both the A/P and sagittal images using the following equations:

$$\begin{bmatrix} x_{cat} & x_{cab} \\ y_{cat} & y_{cab} \\ z_{cat} & z_{cab} \\ 1 & 1 \end{bmatrix} = [REG_A] \begin{bmatrix} Vx_{wt} & Vx_{wh} \\ Vy_{wt} & Vy_{wh} \\ Vz_{wt} & Vz_{wh} \\ 1 & 1 \end{bmatrix}$$

$$\begin{bmatrix} x_{cst} & x_{csb} \\ y_{cst} & y_{csh} \\ z_{cst} & z_{csh} \\ 1 & 1 \end{bmatrix} = [REG_S] \begin{bmatrix} Vx_{wt} & Vx_{wh} \\ Vy_{wt} & Vy_{wh} \\ Vz_{wt} & Vz_{wh} \\ 1 & 1 \end{bmatrix}$$

APPENDIX
(Page 3 of 6)

$$u_{at} = \frac{x_{cat}}{z_{cat}} f \qquad v_{at} = \frac{y_{cat}}{z_{cat}} f$$

$$u_{st} = \frac{x_{cst}}{z_{cst}} f \qquad v_{st} = \frac{y_{cst}}{z_{cst}} f$$

$$u_{ab} = \frac{x_{cab}}{z_{cab}} f \qquad v_{ab} = \frac{y_{cab}}{z_{cab}} f$$

$$u_{sb} = \frac{x_{csb}}{z_{csb}} f \qquad v_{sb} = \frac{y_{csb}}{z_{csb}} f$$

Due to the distortion in fluoroscopic images the projected guidewire is drawn as a curve. This is done by *un-calibrating* 20 points on the line bound by $(u_{at}, v_{at})$ and $(u_{ab}, v_{ab})$ as in [15] and drawing a polyline through them on the A/P image and similarly for the Sagittal image using $(u_{st}, v_{st})$ and $(u_{sb}, v_{sb})$.

[8] To draw the virtual guidewire's projection, two points $(0, 0, 0)$ and $(0, 0, -screwlength)$, in the WCS are transformed so that the top point $(0, 0, 0)$ lies on the line of sight. The virtual guidewire is initially set to 30mm. The projected guidewire is drawn using the following math:

initially:
*depth* = 0.2
*screwlength* = 30mm
$\alpha = 0, \beta = 0$
$(tx, ty, tz)$ is constrained to lie on the line of sight bound by $(LSx_{w1}, LSy_{w1}, LSz_{w1})$ and $(LSx_{w2}, LSy_{w2}, LSz_{w2})$, thus $tx = LSx_{w1} - depth*(LSx_{w2} - LSx_{w1})$
$ty = LSy_{w1} - depth*(LSy_{w2} - LSy_{w1})$
$tz = LSz_{w1} - depth*(LSz_{w2} - LSz_{w1})$ $$\begin{bmatrix} Vx_{wt} & Vx_{wb} \\ Vy_{wt} & Vy_{wb} \\ Vz_{wt} & Vz_{wb} \\ 1 & 1 \end{bmatrix} = [\mathrm{T}^1(\alpha, \beta, tx, ty, tz)] \begin{bmatrix} 0_{wt} & 0_{wb} \\ 0_{wt} & 0_{wb} \\ 0_{wt} & -screwlength_{wb} \\ 1 & 1 \end{bmatrix}$$

in order to draw the projected guidewire on the images, the points $(Vx_{wt}, Vy_{wt}, Vz_{wt})$ and $(Vx_{wb}, Vy_{wb}, Vz_{wb})$ are used in conjunction [7].

[9] Recall that the virtual guidewire is a 3D object bound by $(0_{wt}, 0_{wt}, 0_{wt})$ and $(0_{wb}, 0_{wb}, -screwlength_{wb})$.

*depth* = *depth* + 0.1 * (# pixels moved by the trackball)

$tx = LSx_{w1} - depth*(LSx_{w2} - LSx_{w1})$
$ty = LSy_{w1} - depth*(LSy_{w2} - LSy_{w1})$
$tz = LSz_{w1} - depth*(LSz_{w2} - LSz_{w1})$

---

[1] T is composed of the following transformations:
T = Trans(tx, ty, tz) Rot(y, $\alpha$) Rot(x, $\beta$)
or $$[\mathrm{T}(\alpha, \beta, tx, ty, tz)] = \begin{bmatrix} \cos\alpha & \sin\alpha\sin\beta & \sin\alpha\cos\beta & tx \\ 0 & \cos\beta & -\sin\beta & ty \\ -\sin\alpha & \cos\alpha\sin\beta & \cos\alpha\cos\beta & tz \end{bmatrix}$$

APPENDIX
(Page 4 of 6)

$$\begin{bmatrix} Vx_{wt} & Vx_{wh} \\ Vy_{wt} & Vy_{wh} \\ Vz_{wt} & Vz_{wh} \\ 1 & 1 \end{bmatrix} = [T^1(\alpha, \beta, tx, ty, tz)] \begin{bmatrix} 0_{wt} & 0_{wh} \\ 0_{wt} & 0_{wh} \\ 0_{wt} & -screwlength_{wh} \\ 1 & 1 \end{bmatrix}$$

[10] Recall that the virtual guidewire is a 3D object bound by $(0_{wt}, 0_{wt}, 0_{wt})$ and $(0_{wh}, 0_{wh}, -screwlength_{wh})$.

$\alpha = \alpha + 0.1 *$ (# pixels moved by the trackball)

$$\begin{bmatrix} Vx_{wt} & Vx_{wh} \\ Vy_{wt} & Vy_{wh} \\ Vz_{wt} & Vz_{wh} \\ 1 & 1 \end{bmatrix} = [T^1(\alpha, \beta, tx, ty, tz)] \begin{bmatrix} 0_{wt} & 0_{wh} \\ 0_{wt} & 0_{wh} \\ 0_{wt} & -screwlength_{wh} \\ 1 & 1 \end{bmatrix}$$

[11] Recall that the virtual guidewire is a 3D object bound by $(0_{wt}, 0_{wt}, 0_{wt})$ and $(0_{wb}, 0_{wb}, -screwlength_{wb})$.

$$\begin{bmatrix} Vx_{wt} & Vx_{wb} \\ Vy_{wt} & Vy_{wb} \\ Vz_{wt} & Vz_{wb} \\ 1 & 1 \end{bmatrix} = [T^1(\alpha, \beta, tx, ty, tz)] \begin{bmatrix} 0_{wt} & 0_{wb} \\ 0_{wt} & 0_{wb} \\ 0_{wt} & -screwlength_{wb} \\ 1 & 1 \end{bmatrix}$$

[12] Given $$[T_{ool}]^2 = [Rot_{(z, -90)}][Rot_{(y, -90)}]$$
$$[P_{lan}]^2 = [Rot_{(y,\alpha)}][Rot_{(x,\beta)}][T_{ool}]$$
$$[A_{pproach}]^2 = [Rot_{(z,\gamma)}]$$
$$[F_{inal}P_{lan}]^2 = \begin{bmatrix} P_{Nx} & ? & ? \\ P_{Ny} & & \\ P_{Nz} & & \end{bmatrix}$$

and using the following contraints I determine the remaining two vectors that would be complete [FP].
Note: The first vector (N) is maintained from the [Plan] since it is the dirll guide axis:

Contraints:

1) $FP_{Ax}^2 + FP_{Ay}^2 + FP_{Az}^2 = 1$
2) $A_N \cdot FP_A = 0$
3) $FP_N \cdot FP_A = 0$ $$D = -\frac{A_{Ny}(A_{Nz} \cdot FP_{Nx} - FP_{Nz} \cdot A_{Nx})}{A_{Nx}(FP_{Nx} \cdot A_{Ny} - A_{Nx} \cdot FP_{Ny})} - \frac{A_{Nz}}{A_{Nx}}$$

$$E = \frac{(A_{Nz} \cdot FP_{Nx} - FP_{Nz} \cdot A_{Nx})}{(FP_{Nx} \cdot A_{Ny} - A_{Nx} \cdot FP_{Ny})}$$

---

[2] These matrices are of the following form:
$$\begin{bmatrix} Nx & Ox & Ax \\ Ny & Oy & Ay \\ Nz & Oz & Az \end{bmatrix}$$

APPENDIX
(Page 5 of 6)

$FP_{Az} = \pm\sqrt{D^2 + E^2 + 1}$
$FP_{Ax} = D \cdot FP_{Az}$
$FP_{Ay} = E \cdot FP_{Az}$ $FP_O$ is determined using $FP_O = FP_N \times FP_A$ Hence, $$[\mathbf{FinalPlan}] = \begin{bmatrix} P_{Nx} & FP_{Ox} & FP_{Ax} \\ P_{Ny} & FP_{Oy} & FP_{Ay} \\ P_{Nz} & FP_{Oz} & FP_{Az} \end{bmatrix}$$

Since the PUMA 560 robot uses an Euler representation for specifying an orientation, the inverse solution of [FP] is determined in the following manner:

Euler representation = $Rot(z,\phi)$ $Rot(y, \theta)$ $Rot(z, \psi)$ thus from [i].

$\phi = \arctan(FP_{Ay}, FP_{Ax})$
$\theta = \arctan(FP_{Ax} \cdot \cos(\phi) + FP_{Ay} \cdot \sin(\phi), FP_{Az})$
$\psi = \arctan(-FP_{Nx} \cdot \sin(\phi) + FP_{Ny} \cdot \cos(\phi), -FP_{Ox} \cdot \sin(\phi) + FP_{Oy} \cdot \cos(\phi))$ Adding a PUMA specific offset to $\phi$, and $\theta$ the final position and orientation is established Final pose = $(\phi + 90, \theta - 90, \psi, tx, ty, tz)$

[13] The calibrated coordinates $(x, y)$ of the edge-pixels $(u, v)$ are determined using a quartic polynomial equation as follows:

$x = a_0 u^4 v^4 + a_1 u^4 v^3 + a_2 u^4 v^2 + ... + a_{23} uv + a_{24}$
$y = a_0 u^4 v^4 + a_1 u^4 v^3 + a_2 u^4 v^2 + ... + a_{23} uv + a_{24}$ the set of parameters $a$ and $b$, are previously determined using the image calibration program.

[14] The center of the fiducial shadow is found by fitting the equation of a circle to the edge-pixels using a pseudo-inverse approach:

$$\begin{bmatrix} x_0^2 + y_0^2 \\ \vdots \\ x_n^2 + y_n^2 \end{bmatrix} = \begin{bmatrix} x_0 & y_0 & 1 \\ \vdots & \vdots & \vdots \\ x_n & y_n & 1 \end{bmatrix} \begin{bmatrix} 2h \\ 2k \\ r^2 - h^2 - k^2 \end{bmatrix}$$

or $A = BP$ using pseudo inverse $P = (B^T B)^{-1} B^T A$ once P is established the center of the fiducials $(h, k)$ is determined as follows:

APPENDIX
(Page 6 of 6)

$$h = \frac{p_0}{2}$$

$$k = \frac{p_1}{2}$$

[15] The un-calibrated (distorted) coordinates $(u, v)$ corresponds to the calibrated coordinate $(x, y)$ and is determined using a quartic polynomial equation as follows:

$$u = a_0 x^4 y^4 + a_1 x^4 y^3 + a_2 x^4 y^2 + \ldots + a_{23} xy + a_{24}$$
$$v = a_0 x^4 y^4 + a_1 x^4 y^3 + a_2 x^4 y^2 + \ldots + a_{23} xy + a_{24}$$

the set of parameters $a$ and $b$, are previously determined using a separate calibration program.

---

[i] <u>Robot Manipulators: Mathematics, Programming, and Control</u>; Richard P. Paul; The MIT Press, Cambridge, Massachusetts and London, England, 1983.

What is claimed is:

1. A computer-aided method for planning a surgical procedure comprising:
   registering to a known coordinate frame a first two-dimensional, image of a body's anatomy taken at a first observation angle;
   displaying the first image; and
   drawing in the displayed first image a representation of a surgical object to be placed in the body based on the registration of the first image with the known coordinate frame.

2. The method of claim 1 wherein drawing in the displayed first image the representation of the surgical object is in response to a user indicating at least one positioning parameter for the surgical object.

3. The method of claim 2 wherein the at least one positioning parameter for the surgical object is defined in reference to the known coordinate frame.

4. The method of claim 3 wherein the at least one parameter includes an approach angle of the surgical object.

5. The method of claim 2 wherein the at least one parameter is defined in reference to the first image.

6. The method of claim 5 wherein the at least one parameter includes a point in the body.

7. The method of claim 5 wherein the user indicates the at least one parameter by positioning a cursor displayed within the first image.

8. The method of claim 1 wherein a user indicates at least one parameter defining the surgical object.

9. The method of claim 8 wherein the at least one parameter includes a dimension of the surgical object.

10. The method of claim 1 further comprising:
    registering to the known coordinate frame a second two-dimensional, image of the body's anatomy taken at a second observation angle;
    displaying the second image; and
    drawing in the displayed second image the representation of the surgical object based on the registration of the second image with the known coordinate frame.

11. The method of claim 10 wherein drawing the representation of the surgical object in the second image is in response to a user indicating on the displayed first image indicating a change in position of the representation of the surgical object in the first image.

12. The method of claim 1, wherein the representation of the surgical object is a virtual guidewire defining, at least in part, a trajectory of insertion of the surgical object into the body.

13. The method of claim 1, wherein the representation of the surgical object is a virtual guidewire having a length corresponding to a dimension of the surgical object to be inserted into the body.

14. The method of claim 1 further comprising transmitting to a positioning mechanism coordinates for indicating the position of the surgical object represented in the first image.

15. The method of claim 14 further comprising manipulating the positioning mechanism such that a guide coupled to the positioning mechanism is substantially aligned with the representation of the surgical object in the image.

16. The method of claim 1 further comprising displaying information for indicating the position of the surgical object represented in the first image.

17. A computer readable storage medium encoded with instructions, which, when read by a computer, enable a computer to undertake a process comprising:
    registering to a known coordinate frame a first two-dimensional, image of a body's anatomy taken at a first observation angle;
    displaying the first image; and
    drawing in the displayed first image a representation of a surgical object to be placed in the body based on the registration of the first image with the known coordinate frame.

18. The computer readable storage medium of claim 17 wherein drawing in the displayed first image the representation of the surgical object is in response to a user indicating at least one positioning parameter for the surgical object.

19. The computer readable storage medium of claim 18 wherein the at least one positioning parameter for the surgical object is defined in reference to the known coordinate frame.

20. The computer readable storage medium of claim 19, wherein the indication of the at least one positioning parameter is a reference on the displayed first image controlled by a user.

21. The computer readable storage medium of claim 17 wherein the process further comprises:
    registering to the known coordinate frame a second two-dimensional, image of the body's anatomy taken at a second observation angle;
    displaying the second image; and
    drawing in the displayed second image the representation of the surgical object based on the registration of the second image with the known coordinate frame.

22. The computer readable storage medium of claim 21 wherein drawing the representation of the surgical object in the second image is in response to an input received from a user indicating a position of the surgical object.

23. The computer readable storage medium of claim 21 wherein drawing the representation of the surgical object in the second image is in response to an input received from a user indicating a position of the representation of the surgical object in the displayed first image.

24. The computer readable storage medium of claim 21 wherein drawing the representation of the surgical object in the second image is in response to an input indicating a change in position of the representation of the surgical object in the first image.

25. The computer readable storage medium of claim 21 wherein registering to the known coordinate frame the first image and the second image includes registering known coordinates of a plurality of fiducials within the reference frame with positions of the plurality of fiducials in the first and second images.

26. A computer-aided method for planning a surgical procedure comprising:
    registering a first two-dimensional, image of a body's anatomy taken at a first observation angle with a second two-dimensional image of the body's anatomy taken at a second observation angle;
    displaying the first image;
    drawing within the displayed first image drawing within the displayed first image a representation of a surgical object to be placed in the body based on an input indicating a position of the surgical object;
    displaying the second image; and
    drawing in the displayed second image the representation of the surgical object.

27. The method of claim 26 wherein drawing the representation of the surgical object in the second image is based, at least in part, on positioning in the displayed first image of the representation of the surgical object in the first image.

28. The method of claim 26 wherein drawing in the first image and drawing second image the representation the surgical object is at least in part in response to a user indicating at least one positioning parameter for the surgical object.

29. The method of claim 28 wherein the at least one positioning parameter for the surgical object is defined in reference to a known coordinate frame to which the first and the second images are registered.

30. The method of claim 28 wherein the at least one parameter includes an approach angle of the surgical object.

31. The method of claim 28 wherein the at least one parameter includes a point in the body.

32. The method of claim 28 wherein the user indicates the at least one parameter by positioning a reference displayed within the first or second images.

33. The method of claim 26 wherein a user indicates at least one parameter defining the surgical object.

34. The method of claim 26 further comprising transmitting to a positioning mechanism coordinates for indicating the position of the surgical object represented in the first image.

35. The method of claim 34 further comprising manipulating the positioning mechanism such that a guide coupled to the positioning mechanism is substantially aligned with the representation of the surgical object in the image.

36. The method of claim 26 further comprising displaying information for indicating the position within a known coordinate frame of reference for the surgical object for use in manually positioning a guide.

37. The method of claim 26 wherein registering the first and second images includes registering a plurality of fiducials having known coordinates within a known coordinate frame of reference with images of the plurality of fiducials within in the respective first and second images.

38. A computer readable storage medium encoded with instructions, which, when read by a computer, enable a computer to undertake a process comprising:
   receiving a first two-dimensional, image taken of a patient's body and a plurality of radio-opaque fiducials placed adjacent the body at known positions; and
   registering the image by optimizing parameters of a known geometric model such that projections of the plurality of fiducials into the first image best fit positions of the plurality of fiducials in the image.

39. The computer readable storage medium of claim 38, wherein the process further comprises:
   receiving a second, two-dimensional image taken of the patient's body and the plurality of fiducials from a position different from the first image; and
   registering the second image by optimizing parameters of the known geometric model such that projections of the plurality of fiducials into the second image best fit positions of the plurality of fiducials in the second image.

40. The computer readable storage medium of claim 39, wherein the process further comprises:
   receiving input indicating on one of the first and second images a position of a representation of an imaginary object with respect to the body; and
   drawing on the other of the first and second images a corresponding representation of the imaginary object projected into said other of the first and second images.

41. The computer readable storage medium of claim 40 further comprising:
   receiving input indicating a change to a second position of the representation of the imaginary object within said one of the first and second image; and
   redrawing within said other of the first and the second images the corresponding representation of imaginary object in the second position.

42. The computer readable storage medium of claim 40 wherein the imaginary object is a representation of a surgical object and the corresponding representation is also of the same surgical object.

43. The computer readable storage medium of claim 39, wherein the process further comprises:
   receiving an input indicating a position of an imaginary object within the body; and
   drawing on the first and the second images a representation of the imaginary object in the indicated position.

44. The computer readable storage medium of claim 43, wherein the process further comprises:
   receiving an input indicating a change in the position of the imaginary object to a second position; and
   redrawing in the first and the second images the representation of imaginary object in the second position.

45. The computer readable storage medium of claim 38, wherein registering the image further comprises:
   displaying the image; and
   receiving an input from a user indicating on the image the position of each of the plurality of fiducials within the image.

46. The computer readable storage medium of claim 38, wherein the process further comprises linearizing the image before registering the image.

47. A method comprising:
   receiving a first two-dimensional, image taken of a patient's body and a plurality of radio-opaque fiducials placed adjacent the body at known positions; and
   registering the image by optimizing parameters of a known geometric model such that projections of the plurality of fiducials into the first image best fit positions of the plurality of fiducials in the image.

48. The method of claim 47 further comprising:
   receiving a second, two-dimensional image taken of the patient's body and the plurality of fiducials from a position different from the first image; and
   registering the second image by optimizing parameters of the known geometric model such that projections of the plurality of fiducials into the second image best fit positions of the plurality of fiducials in the second image.

49. The method of claim 48 further comprising:
   receiving input indicating on one of the first and second images a position of a representation of an imaginary object with respect to the body; and
   drawing on the other of the first and second images a corresponding representation of the imaginary object projected into said other of the first and second images.

50. The method of claim 49 further comprising:
   receiving input indicating a change to a second position of the representation of the imaginary object within said one of the first and second image; and
   redrawing within said other of the first and the second images the corresponding representation of imaginary object in the second position.

51. The method of claim 49 wherein the imaginary object is a representation of a surgical object and the corresponding representation is also of the same surgical object.

52. The method of claim 48 further comprising:

receiving an input indicating a position of an imaginary object within the body; and drawing on the first and the second images a representation of the imaginary object in the indicated position.

53. The method of claim 52 further comprising:

receiving an input indicating a change in the position of the imaginary object to a second position; and redrawing in the first and the second images the representation of imaginary object in the second position.

54. The method of claim 47 further comprising:

displaying the image; and receiving an input from a user indicating on the image the position of each of the plurality of fiducials within the image.

55. The method of claim 47 further comprising linearizing the image before registering the image.

* * * * *